United States Patent
Mershin et al.

(10) Patent No.: US 12,344,877 B2
(45) Date of Patent: Jul. 1, 2025

(54) SYNELL CREATION, EVOLUTION, AND DIGITAL TRANSMISSION

(71) Applicant: Massachusetts Institute of Technology, Cambridge, MA (US)

(72) Inventors: Andreas Mershin, Cambridge, MA (US); Katarzyna Paulina Adamala, Minneapolis, MN (US)

(73) Assignee: Massachusetts Institute of Technology, Cambridge, MA (US)

( * ) Notice: Subject to any disclaimer, the term of this patent is extended or adjusted under 35 U.S.C. 154(b) by 32 days.

(21) Appl. No.: 17/866,455

(22) Filed: Jul. 15, 2022

(65) Prior Publication Data
US 2023/0295680 A1 Sep. 21, 2023

Related U.S. Application Data

(63) Continuation of application No. 15/831,379, filed on Dec. 4, 2017, now abandoned.

(60) Provisional application No. 62/429,787, filed on Dec. 3, 2016.

(51) Int. Cl.
*C12P 21/00* (2006.01)
(52) U.S. Cl.
CPC .................... *C12P 21/00* (2013.01)
(58) Field of Classification Search
CPC .................................. B01J 19/0093
See application file for complete search history.

(56) References Cited

PUBLICATIONS

Wu, Nan, et al. "A PMMA microfluidic droplet platform for in vitro protein expression using crude *E. coli* S30 extract." Lab on a Chip 9.23 (2009): 3391-3398. (Year: 2009).*

* cited by examiner

*Primary Examiner* — Robert J Yamasaki
(74) *Attorney, Agent, or Firm* — Norma E. Henderson

(57) ABSTRACT

Synells are created by encapsulating components and iteratively optimizing each synell for a desired trait. Each synell is tested during each interation. Failed synells are discarded. Additional synell components are added during each iteration, with iterative optimization being repeated until synells having the trait are created. A method for synell reproduction includes creating a synell having a desired trait, determining a recipe for the synell, digitizing the recipe, and transmitting the digitized recipe to another location. The recipe is reconstituted at the other location and the synell is reproduced using the recipe. On-demand biosynthesis of synells includes generating droplets containing different synell components within a microfluidic device, fusing them into combinations, and storing them until a request for a synell having a particular trait is received. Fused droplets having the component combination for the trait, or being combinable to produce it, are retrieved and encapsulated to form the requested synell.

8 Claims, 11 Drawing Sheets

SYNELL CREATION, EVOLUTION, AND DIGITAL TRANSMISSION

RELATED APPLICATIONS

This application is a continuation of U.S. patent application Ser. No. 15/831,379, filed Dec. 4, 2017, which claims the benefit of U.S. Provisional Application Ser. No. 62/429,787, filed Dec. 3, 2016, the entire disclosures of which are herein incorporated by reference.

STATEMENT REGARDING FEDERALLY SPONSORED RESEARCH OR DEVELOPMENT

This invention was made with U.S. Government Support under Grant Number HR0011-12-1-0003, awarded by the Defense Advanced Projects Research Agency. The U.S. Government has certain rights in this invention.

FIELD OF THE TECHNOLOGY

The present invention relates to biosynthesis and, in particular, to bottom-up assembled bio- and chemo-reactors (synells).

BACKGROUND

Synthetic cells and cell-sized bio- and chemo-reactors built from chemical and enzymatic components (synells) are an increasingly popular tool for studying biochemical reactions, manufacturing biomolecules, investigating past and present biology, and building bio-orthogonal sensor devices. On-demand biosynthesis is of particular interest. The best known example of a transformative biosynthesis approach using traditional techniques is that of the anti-malaria agent Atremisinin.

Synells are distinct from, but complemented by, 84 years of development of various other synthetic cell technologies, from the first mention of the concept in 1932 [Crile, G., Telkes, M. & Rowland, A. F., "Autosynthetic cells", Protoplasma 15, 337-360 (1932)] until the most recent advancements [Xu, C., Hu, S. & Chen, X., "Artificial cells: from basic science to applications", Mater. Today 00, (2016)]. Creating synthetic life has been proposed as an approach that could help improve understanding of natural biology, engineer biologically-relevant systems for biomanufacturing, and elucidate the origin and earliest evolution of life [Porcar, M. et al., "The ten grand challenges of synthetic life", Syst. Synth. Biol. 5, 1-9 (2011); Elowitz, M. & Lim, W. a., "Build life to understand it", Nature 468, 889-890 (2010)].

In 1932, structures made of "protein and lipid constituents from physiological materials" were described, suggesting use of such "autosynthetic cells" as model systems for living cells. All of the major expression systems used today were developed very early in the history of this technology. In 1954, the first cell-free protein synthesis was demonstrated, using rat liver cells [Luisi, P. L., Walde, P. & Oberholzer, T., "Enzymatic RNA synthesis in self-reproducing vesicles: An approach to the construction of a minimal synthetic cell", Berichte der Bunsengesellschaft für Phys. Chemie 98, 1160-1165 (1994)]. In 1961, a bacterial system was developed [Noireaux, V. & Libchaber, A., "A vesicle bioreactor as a step toward an artificial cell assembly", Proc. Natl. Acad. Sci. U.S.A. 101, 17669-74 (2004)], followed by a plant extract in 1973 [Zawada, J. F. et al., "Microscale to manufacturing scale-up of cell-free cytokine production—a new approach for shortening protein production development timelines", Biotechnol. Bioeng. 108, 1570-1578 (2011)] and yeast in 1979 [Guan, H., Liu, X. & Wang, W., "Encapsulation of tyrosinase within liposome bioreactors for developing an amperometric phenolic compounds biosensor", J. Solid State Electrochem. 17, 2887-2893 (2013)]. In 1988, a continuous reactor was demonstrated, enabling high-yield preparative scale reactions [Luisi, P. L. & Stano, P., "Synthetic biology: Minimal cell mimicry", Nat. Chem. 3, 755-756 (2011)]. The most commonly used system today, the T7 polymerase system, was introduced in 1991 [Dignam J D, Lebovitz R M, R. R., Dignam, J. D., Lebovitz, R. M., Roeder, R. G., "Accurate transcription initiation by RNA polymerase II in a soluble extract from isolated mammalian nuclei", Nucleic Acids Res. 1, 1475-1489 (1983)]. The term "synthetic minimal cell" was first used in 1994 to describe replication of RNA in liposomes [Stano, P. & Luisi, P. L., "Semi-synthetic minimal cells: Origin and recent developments", Curr. Opin. Biotechnol. 24, 633-638 (2013)]. The term "synell" has now been introduced as an encompassing top level category that includes the synthetic minimal cells of the past as well as other more recently developed technologies. In 2001, the PURE expression system was developed [Yollete V. Guillen Schlippe, Matthew C. T. Hartman, Kristopher Josephson, and J. W. S., "In Vitro Selection of Highly Modified Cyclic Peptides That Act as Tight Binding Inhibitors", J. Am. Chem. Soc. 134, (2012)]. The first synthetic cell (synell) expressing proteins inside liposomes was described in 2004 [Elani, Y., Law, R. V. & Ces, O., "Vesicle-based artificial cells as chemical microreactors with spatially segregated reaction pathways", Nat. Commun. 5, 5305 (2014)]. In 2011, cell-free protein synthesis entered industrial scale with >100l reactors, and the year 2014 saw the first demonstration of communication between synthetic and natural cells [Karig, D. K., Iyer, S., Simpson, M. L. & Doktycz, M. J., "Expression optimization and synthetic gene networks in cell-free systems", Nucleic Acids Res. 40, 3763-3774 (2012)].

The creation of a living cell functioning on an entirely chemically synthesized genome [Bedau M, Church G, Rasmussen S, Caplan A, Benner S, Fussenegger M, Collins J, D. D., "Life after the synthetic cell", Science 465, 422-424 (2010); Gibson, D. G. et al., "Creation of a bacterial cell controlled by a chemically synthesized genome", Science 329, 52-56 (2010); Hutchison, C. a. et al., "Design and synthesis of a minimal bacterial genome" Science (80-.). 351, aad6253-aad6253 (2016)], has led to further efforts aimed at discovering minimal subsets of genes necessary for the continued survival of naturally-occurring cells [Gil, R., Silva, F. J., Peretó, J. & Pereto, J., "Determination of the Core of a Minimal Bacterial Gene Set", Microbiol. Mol. Biol. Rev. 68, 518-537 (2004); Moya, A. et al., "Toward minimal bacterial cells: Evolution vs. design", FEMS Microbiol. Rev. 33, 225-235 (2009)]. By removing as many genes as possible from *M. mycoides*, these efforts aim at building a minimal biological cell or "cell chassis" which is derived from a cell originally occurring in nature. Such an approach allows a better understanding of the functions of an essential remaining gene set and provides a versatile toolkit for studying biology [Shimizu, Y. et al. "Cell-free translation reconstituted with purified components", Nat. Biotechnol. 19, 751-5 (2001)] in general, with applications to biomanufacturing and simplified metabolic pathway engineering in particular. This approach is distinctly different from synell technology, even though in some cases the final goals of both methodologies might be identical.

SUMMARY

The invention is a method and apparatus for creating synells and analogues, and for iteratively optimizing and evolving them, as well as for transmitting the information for re-creating synells away from the original site of optimization. It provides methods for leveraging bottom-up assembled bio- and chemo-reactors (synells) to overcome the limitations of cell-based biosynthesis methods.

In one aspect, the invention comprises a novel modular, generalizable microfluidic, mesofluidic, 3D-printing, and droplet generation, with optional electrospinning capabilities, platform applied together with a cell-free expression system encapsulated in liposomes or other vesicle assemblies that include a modular gene library to allow iterative metabolic and other cell-analogue optimization. In another aspect, the invention includes the methods used in preparing the different types of synells.

In one aspect, the invention is a method for creating ensembles of identical synells that includes encapsulating at least one synell component within each of a plurality of synell compartments to create a plurality of synells and then iteratively optimizing each synell for a prespecified trait by performing an iterative optimization cycle. The synell is tested for compliance with an intermediate state. If the synell fails the test, the failed synell is removed from the iterative optimization cycle. If the synell passes the test, at least one additional synell component is added to the synell. The iterative optimization cycle is repeated until a desired number of synells having the desired trait have been created. In some embodiments, the interative optimization cycle may be under computer control, and may take place in a microfluidic device. In some embodiments, testing may be carried out via flow cytometry. In some embodiments, adding components may employ at least one microfluidic droplet injector. In some embodiments, the trait is synell function or composition.

In another aspect, the invention is a method for synell reproduction that includes creating a synell having a desired trait, determining a recipe for the synell, digitizing the determined recipe and then performing at least one of storing the digitized recipe electronically at the current location and transmitting the digitized recipe to, and receiving it at, at least one other location. The method further includes retrieving the digitized recipe, reconstituting the determined recipe from the digitized recipe at the current and/or other locations, and reproducing the synell by creating at least one new synell using the reconstituted determined recipe. In some embodiments, iterative design optimization ie employed to create a synell having the desired trait. In some embodiments, the trait is synell function or composition.

In yet another aspect, the invention is a method for on-demand biosynthesis of synells, including generating a plurality of droplets or liposomes containing different synell components within a microfluidic device; fusing the generated droplets or liposomes into a plurality of prespecified component combinations; storing the fused droplets or liposomes separately within a microfluidic storage device; and recording the location within the microfluidic storage device of fused droplets or liposomes having each type of component combination. Upon receiving a request for a synell having a particular trait, fused droplets or liposomes that have the component combination for the requested synell or that may be combined to produce the requested synell are retrieved from the microfluidic storage device and encapsulated to form at least one requested synell.

BRIEF DESCRIPTION OF THE DRAWINGS

Other aspects, advantages and novel features of the invention will become more apparent from the following detailed description of the invention when considered in conjunction with the accompanying drawings, wherein.

DETAILED DESCRIPTION

Figure 2:
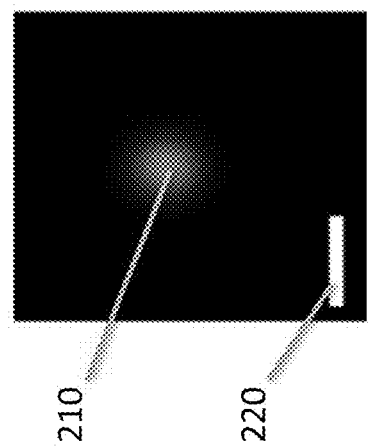
FIG. 2 is a photograph showing an implemented synell expressing green fluorescent protein (GFP) under T7 promotor, using *E. coli* transcription-translation mix.

Synells according to the invention are bottom-up assembled bioreactors and/or chemo-reactors capable of expressing proteins via transcription and translation (TX-TL) reactions similar to those taking place in naturally-occurring cells. They range in size from sub-micron to milimeter, and are assembled from pre-made components by adding the molecular machinery and reactants required for transcription and translation (such as enzymes, cofactors, substrates) into vessels such as liposomes or droplets. The function of this is to separate the transcription-translation system operational substrates and products from the environment, under well-controlled reproducible conditions.

As used herein, the following terms expressly include, but are not to be limited to:

"Synell" means any artificially-created cell-sized vessel wherein a biological or chemical series of reactions can take place. The components within synells may be artificially-created and/or may be naturally-occurring or naturally-derived, and may be mixed and matched according to the intended function or application of the synell. A synell is to be distinguished from a minimal living cell (Venter organism), because it is built from non-living components, rather than being derived directly from another living cell.

"Cell-sized" means roughly between sub-micron diameter and single millimeter diameter for the case of spherical synells and volumes between 0.1 cubic microns (0.1 attoliters) and 1 cubic centimeter (1 milliliter).

"Synell technology" means any technology employed to create, evolve, transmit, test, manipulate, or apply synells. For example, each of the following is a "synell technology": (a) an apparatus configured to generate synells such as a microfluidic bubble maker, a single or double emulsion maker, a droplet generator, (b) an apparatus configured to select synells from a stream based on a user-defined set of characteristics, (c) an apparatus configured to fuse or co-locate synells, cells, and other materials from various sources, (d) an apparatus configured to perform synell isolation in a manner similar to cell flow-cytometry, (e) an apparatus configured to store synells in specific locations, (f) an apparatus configured to add amino acid, nucleic acid, organic or inorganic components to be encapsulated by synells, such as by counting droplets each containing a set number of genes per droplet or a known concentration of substrate, ATP, nanomaterial, or other TX/TL machinery, and (g) an apparatus configured to screen conditions for synell generation, including size and composition of synells. While specific examples of "synell technology" are presented here for explanatory purposes, it will be clear to one of skill in the art that many other examples exist and are included within the scope of this definition.

As a specific example, a "synell technology" may include multiple droplet generators, under the control of feedback loops that may be themselves partially controlled by the input from multiple sensors such as temperature, pH, turbidity, optical density, salinity, dissolved oxygen, or other gas concentrations, results of machine olfactors in wet or dry phase, mass-spectrometry gas chromatography, fluorescence, and other such measurements coupled to processors and signal processing and signal acquisition apparatus operating separately or in unison for the exploration of conditions, amplification of yields, discovery of new products, and rapid prototyping of biosynthetic and chemosynthetic pathways. For example, a synell technology may be used in conjunction with a machine olfactor (or trained human) to match a scent conferred by a known "target" volatile mixture in a gaseous environment (such as a fragrance) to that generated by synells containing odorant expression pathways, or to iteratively compare the action of a known drug molecule, or toxin molecule, or mixtures of drugs at various relative concentrations on a pure or multi-strain cell culture or co-culture (such as, for instance, the effects of a chemotherapy drug cocktail on a co-culture of cancer cells and neurons) to the action of products of synthetic pathways that may be constantly shuffled (screened) and delivered by a stream of synells containing different variations of biosynthetic machinery. Such screening may continue until an image processor or other assayer determines the effects of the known drug and the products of a synell-borne pathway to be indistinguishable, at which point the pathway that was found to create the desired result can be amplified using the same synell technology and apparatus by switching from "discovery" to "production" modes by simply repeating the production of the synell contents that led to the desired outcome.

The concept of removing cellular components to form a minimal cell is herein termed as being "top down" and is fundamentally different from the present invention, which is synells that are created "bottom up". Top-down cell-based approaches depend on stripping down a naturally occurring cell to establish minimum genomes and proteome types necessary to continue growth and division [Shimizu, Y. et al., "Cell-free translation reconstituted with purified components", Nat. Biotechnol. 19, 751-5 (2001)], at least in petri dishes if not in the wild. By contrast, the "bottom-up" approach of forming synells according to the invention does not assume the end goal of a fully autonomous, replicating "biological cell", but rather a biochemical reactor designed and directly assembled from nano- and micro-sized building blocks of synthetic or natural origin (enzymes, lipids, small molecules). Such functional "bottom-up" approach synells may in some cases perform metabolism, growth, reproduction and adaptation, and even be able to survive outside of laboratory conditions, but the impetus behind the invention is not limited to replicating a simplified version of a natural cell. And while similarly to the top-down effort, synells may result in the creation of general-purpose chassis into which gene pathways may be inserted for study and yield optimization, synell technologies according to the invention allow the exploration of physiochemical phase spaces currently unavailable to naturally occurring biochemistry, such as conditions involving high concentrations of reactants or products that would be toxic to a cell-based system, and the separation of cross-interacting enzymatic pathways into individually optimizable steps in physicochemical as well as physical phase space as well as time.

One key difference between the two approaches is in that synells are not required to reproduce unassisted. Unlike minimal cells, which in addition to performing metabolism necessary for the biosynthesis of human-desired products have to also perform their own "housekeeping" and sustain themselves through cycles of cell-division and colony growth, synells can be thought of as disposable "single-use" vessels that can be made in large numbers to create ensembles of identical or mixed "genotypes" and "phenotypes" to perform functions similar to those of traditional biomanufacturing but also new, unfamiliar ones. Currently, most synells do not reproduce and they very rarely grow. In some scenarios, building synells does converge to a biological cell-like model for studying the first principles of biology allowing for the reduction of complex biological systems to the first principle biochemical reactions. "Top-down" minimal cell and "bottom-up" synell direction can be both complementary and orthogonal.

Anatomy of an exemplary synell: cell-free transcription-translation systems.

One function of a preferred embodiment of synells according to the invention is protein synthesis, and one of the most significant advantages of synell technology over live natural cells is the high degree of modularity and control over the protein synthesis reaction. To achieve this function, cell-free protein synthesis systems are used for transcription and translation inside synells. In this example implementation, the synell is comprised of transcription (TX) and translation (TL) enzymes, i.e. the transcription-translation system, encapsulated within a set of boundaries, possibly including optional subcompartments, that insulate it from the environment and create internal sorting structures.

Figure 1:
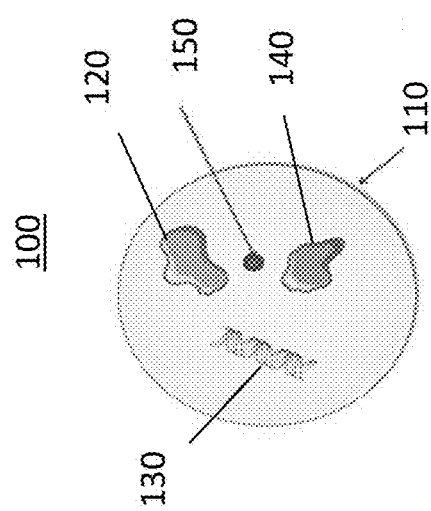
FIG. 1 is a diagram of an example embodiment of a synell, according to one aspect of the invention.

FIG. 1 depicts elements of an example embodiment of a synell, according to one aspect of the invention. As shown in FIG. 1, synell 100 has compartment 110 that encapsulates a protein synthesis system, other enzymes, and small molecules, isolating them from the environment and concentrating reagents. Possible components encapsulated within compartment 110 include, but are not limited to, enzymes and reagents 120, gene expression system 130, substrates 140, and signalizing molecules 140.

FIG. 2 is a photo of an example synell 210 expressing green fluorescent protein (GFP) under T7 promotor, using *E. coli* transcription-translation mix. Scale 220 bar=2.5 µm.

Cell-free transcription/translation (TX/TL) systems can be obtained from many organisms, including, but not limited to, bacteria, yeast, wheat, *Leichmania*, insects, rabbits and other mammals, and humans. As the complexity of the source organism increases, so does the cost and relative ease of use of any given enzyme preparation. While the absolute yield of protein production decreases with increasing complexity of the organism, the relative yield of properly folded, full length protein increases, as the higher clads have more complex and efficient post-translational modifications and folding chaperones. Large and multi-domain proteins may therefore be produced.

The compartmentalization of reagents in synell can be achieved in any of several ways. In some embodiments, bilayer lipid membranes create liposomes, with all enzymes and other reagents of the synell in the lumen, and often membrane proteins serving as channels or receptors. In other embodiments, water/oil emulsions create distinct pools of reagent. In some embodiments, microfluidic devices provide precise control over copy number of genes and other reagents by varying the drop size and by joining drops from separate sources.

The desired properties and applications of synells dictate the design and selection of type of the TX/TL enzyme system used and the manner of isolating it from the outside world. The transcription-translation solution itself may be derived from a lysate of naturally occurring cells, cell-free synthesized, or a mixture of the two pathways.

Cell-free expression systems may come as pre-made commercially available kits, or custom-developed and optimized lysates from bacterial or eukaryotic sources including, but not limited to, mammalian, wheat germ, yeast, and insect sources. When the main desired function of a synell is to express proteins, the type of transcription-translation enzyme mix selected is crucial to the success of the intended applications. Different systems vary in yield, efficiency, ease and cost of use, and the ability to introduce posttranslational modifications.

In some embodiments, the highest level of control over the translation process is achieved by using the purified translation system of *E. coli*, the PURE (Protein synthesis Using Recombinant Elements) system [Yollete V. Guillen Schlippe, Matthew C. T. Hartman, Kristopher Josephson, and J. W. S., "In Vitro Selection of Highly Modified Cyclic Peptides That Act as Tight Binding Inhibitors", J. Am. Chem. Soc. 134, (2012]. The PURE system has the disadvantages of lowest yields and high difficulty and cost, but it offers uniquely precise control and reproducibility, because all proteins involved in the synthesis are purified separately, and all cofactors, tRNA and substrates are added to the mix separately. This system permits the synthesis of modified proteins, changing genetic code, and using unnatural amino acids [Hillebrecht, J. R. & Chong, S., "A comparative study of protein synthesis in in vitro systems: from the prokaryotic reconstituted to the eukaryotic extract-based", BMC Biotechnol. 8, 58 (2008)].

In contrast to the PURE system, whole-cell lysate extracts have been widely used, trading ease-of-use and significantly higher yields at a lower cost per reaction for a lack of precise control over the components of the system, since each protein and small molecule is not purified independently. Both eukaryotic and prokaryotic systems are used as lysate sources, and the advantages and disadvantages of both have been characterized in nuanced detail elsewhere [Gagoski, D. et al., "Performance Benchmarking of four cell-free protein expression systems", Biotechnol. Bioeng. 113 (2015); Zemella, A., Thoring, L., Hoffmeister, C. & Kubick, S., "Cell-Free Protein Synthesis: Pros and Cons of Prokaryotic and Eukaryotic Systems", ChemBioChem (2015); Hino, M. et al., "Efficiency of cell-free protein synthesis based on a crude cell extract from *Escherichia coli*, wheat germ, and rabbit reticulocytes", J. Biotechnol. 133, 183-189 (2008); Endo, Y. & Sawasaki, T., "Cell-free expression systems for eukaryotic protein production", Curr. Opin. Biotechnol. 17, 373-380 (2006); Chang, H. C., Kaiser, C. M., Hartl, F. U. & Banal, J. M., "De novo folding of GFP fusion proteins: High efficiency in eukaryotes but not in bacteria", J. Mol. Biol. 353, 397-409 (2005)].

Generally, eukaryotic systems offer better folding and access to post-translational modifications, at the price of significantly lower yields. When a synell is designed to act as a simple sensor or reactor producing a single peptide without complex post-translational modifications, the prokaryotic system allows for higher yields at lower cost. If multi-domain proteins, complex signaling cascades, or large proteins are needed, eukaryotic systems are typically preferable. Folding of large fusion proteins is much more efficient in eukaryotic systems, due to the presence of folding chaperones [Sun, Z. Z. et al., "Protocols for Implementing an *Escherichia coli* Based TX-TL Cell-Free Expression System for Synthetic Biology", J. Vis. Exp. 1-15 (2013)]. Eukaryotic systems also offer a much wider range of post-translational modifications than prokaryotic extracts [Gagoski, D. et al., "Performance Benchmarking of four cell-free protein expression systems", Biotechnol. Bioeng. 113 (2015)].

The bacterial extract, most commonly prepared from *E. coli*, is robust to changes in reaction temperature and tolerant to chemical additives, offering high yield of simple, unmodified proteins [Caschera, F. & Noireaux, V., "A cost-effective polyphosphate-based metabolism fuels an all *E. coli* cell-free expression system", Metab. Eng. 27, 29-37 (2015); Garamella, J., Marshall, R., Rustad, M. & Noireaux, V., "The all *E. coli* TX-TL Toolbox 2.0: a platform for cell-free synthetic biology", ACS Synth. Biol. acssynbio.5b00296 (2016); Liu, D. V., Zawada, J. F. & Swartz, J. R., "Streamlining *Escherichia Coli* S30 extract preparation for economical cell-free protein synthesis", Biotechnol. Prog. 21, 460-465 (2005); Kigawa, T. et al., "Preparation of *Escherichia coli* cell extract for highly productive cell-free protein expression", J Struct Funct Genomics 5, 63-68 (2004); Harbers, M., "Wheat germ systems for cell-free protein expression", FEBS Lett. 588, 2762-2773 (2014)]. Wheat-germ extracts offer high yields at low cost, but like bacterial extracts, these systems offer no glycosidation or any other post-translational modifications, and can suffer from premature termination of translation [Madin, K., Sawasaki, T., Ogasawara, T. & Endo, Y., "A highly efficient and robust cell-free protein synthesis system prepared from wheat embryos: plants apparently contain a suicide system directed at ribosomes", Proc. Natl. Acad. Sci. U.S.A. 97, 559-564 (2000); Ezure, T. et al., "Cell-Free Protein Synthesis System Prepared from Hi5 Insect Cells by Freeze-Thawing", Biotechnol. Prog 22, 1570-1577 (2006)]. The insect cell-free protein synthesis can be prepared from many different species of moth [Swerdel, M. R. & Fallon, A. M., "Cell-free translation in lysates from *Spodoptera frugiperda* (Lepidoptera: Noctuidae) cells", Comp. Biochem. Physiol. B. 93, 803-6 (1989); Fox, A. S., Kan, J., Kang, S. H. & Wallis, B., "Protein Synthesis in Cell-Free Preparations From Drosophila", J. Biol. Chem. 240, 2059-2065 (1965)] or fly [Scott, M. P., Storti, R. V, Pardue, M. L. & Rich, A., "Cell-free protein synthesis in lysates of Drosophila melanogaster cells", Biochemistry 18, 1588-1594 (1979); Schoborg, J. a., Hodgman, C. E., Anderson, M. J. & Jewett, M. C., "Substrate replenishment and byproduct removal improve yeast cell-free protein synthesis", Biotechnol. J. 9, 630-640 (2014)], offering the ability to translate large proteins while allowing limited protein glycosidation.

The yeast cell-free protein synthesis system offers low cost, high yield synthesis of simple eukaryotic proteins. This system has been recently significantly improved [Gan, R. & Jewett, M. C., "A combined cell-free transcription-translation system from Saccharomyces cerevisiae for rapid and robust protein synthesis", Biotechnol. J. 9, 641-651 (2014); Kovtun, O. et al., "*Leishmania* cell-free protein expression system", Methods 55, 58-64 (2011); Mikami, S., Kobayashi, T., Yokoyama, S. & Imataka, H., "A hybridoma-based in vitro translation system that efficiently synthesizes glycoproteins", J. Biotechnol. 127, 65-78 (2006)]. Unicellular protozoan *Leishmania tarentolae* is one of the most recently suggested sources of efficient, cheap, eukaryotic cell-free protein expression system, including eukaryotic translational and simple folding chaperones, yet it lacks more advanced post-translational machinery [Mikami, S., Kobayashi, T., Masutani, M., Yokoyama, S. & Imataka, H., "A human cell-derived in vitro coupled transcription/translation system optimized for production of recombinant proteins", Protein Expr. Purif. 62, 190-198 (2008)]. There are few different mammalian cell-free protein synthesis systems available. The commercially available rabbit reticulocyte lysate offers cap-independent translation and contains mammalian folding chaperones. The glycosidation of proteins can be achieved in this system upon addition of canine microsomal membranes [Machida, K., Masutan, M. & Imataka, H., "Protein Synthesis in vitro: Cell-Free Systems Derived from Human Cells" (2012)]. This typically decreases overall yield of protein synthesis. Human HeLa cell extract is also commercially available, and is used to express antibodies, large and complex proteins, and viruses [Brödel, A. K. & Kubick, S., "Developing cell-free protein synthesis systems: a focus on mammalian cells", Pharm. Bioprocess. 2, 339-348 (2014); Russ, Z. N. & Dueber, J. E., "Cell-free protein synthesis: Search for the happy middle", Biotechnol. J. 9, 593-594 (2014)].

The bacterial transcription-translation mix is easier to prepare and less expensive than its eukaryotic counterpart, however it does not offer post-translational modifications or the ability to synthesize large, complex proteins. By contrast, the mammalian system is much more expensive to prepare and the protein yield is significantly lower. However, the mammalian system provides synthesis of long, complex proteins that require folding chaperones and post-translational modifications [Pardee, K. et al., "Paper-Based Synthetic Gene Networks", Cell 159, 940-954 (2014)]. Given the high cost and low protein yield of the insect and mammalian systems, the yeast extract has been proposed as a convenient middle-ground solution, maintaining the advantages of large scale preparation and eukaryotic folding chaperones [Smith, M. T., Berkheimer, S. D., Werner, C. J. & Bundy, B. C., "Lyophilized *Escherichia coli*-based cell-free systems for robust, high-density, long-term storage", Biotechniques 56, 186-93 (2014)].

Bacterial transcription-translation systems can enable synells to be used under conditions that are not optimal for many common molecular biology transformations. Some TX/TL systems can be lyophilised[39,40] [Endoh, T. et al., "Cell-free protein synthesis at high temperatures using the lysate of a hyperthermophile", J. Biotechnol. 126, 186-195 (2006); Anderson, M. J., Stark, J. C., Hodgman, C. E. & Jewett, M. C., "Energizing eukaryotic cell-free protein synthesis with glucose metabolism", FEBS Lett. 589, 1723-1727 (2015)], allowing convent long term storage and shipment. Extract of thermophilic bacteria can be used at high temperatures, even up to 80° C. [Matthies, D. et al., "Cell-free expression and assembly of ATP synthase", J. Mol. Biol. 413, 593-603 (2011)].

The transcription-translation extract is typically prepared from lysed cells. To achieve efficient protein synthesis inside synells, consumable substrates (amino acids, nucleotides) need to be supplemented. Notably, this is often also the case for the top-down approach of minimal biological cells, where the missing genes have robbed the original organism of its ability to synthesize nucleic and some amino acids which are spiked in the extra rich medium [Hutchison, C. a. et al., "Design and synthesis of a minimal bacterial genome", Science (80-.). 351, aad6253-aad6253 (2016)]. Also, the energy source is often a limiting factor in cell-free, synell-based transcription-translation reactions. Most typically, the energy substrate can be added into the mix prior to encapsulation inside the synell. Robust methods of supplementing and enhancing availability of high-energy substrates in prokaryotic and eukaryotic [Gan, R. & Jewett, M. C., "A combined cell-free transcription-translation system from Saccharomyces cerevisiae for rapid and robust protein synthesis", Biotechnol. J. 9, 641-651 (2014); Panthu, B., Decimo, D., Balvay, L. & Ohlmann, T., "In vitro translation in a hybrid cell free lysate with exogenous cellular ribosomes", Biochem. J. 398, 387-398 (2015)] systems have been developed. For instance, the ATP synthase complex expressed inside synells provides recycling of the energy source during the reaction [Caschera, F. & Noireaux, V., "Compartmentalization of an all-*E. coli* Cell-Free Expression System for the Construction of a Minimal Cell", Artif. Life 22, 1-11 (2016)].

Typically, the cytoplasmic fraction and ribosomes of a whole-cell extract are used together, providing chaperones, transcription factors, and translation machinery from the same source. Recently, a hybrid system has been developed, with ribosomes and cytoplasmic fraction being purified separately from different organisms and combined for efficient protein synthesis reaction [Spencer, A. C., Torre, P. & Mansy, S. S., "The Encapsulation of Cell-free Transcription and Translation Machinery in Vesicles for the Construction of Cellular Mimics", J. Vis. Exp. 1-7 (2013)]. This approach may permit creating synells by combining properties of protein synthesis systems from different organisms, potentially bypassing some of the current limitations of homogenous systems as well as allowing for the comparative study of structure-function-origin relations of similar mechanisms from different lineages.

Anatomy of a Synell Membrane

Encapsulation of protein synthesis machinery inside synells prevents dilution and controls relative concentrations of reagents, provides a barrier between chemical environments inside and outside of the synell, and allows precise control of gene expression via encapsulation of plasmid coding genes by literally digitizing the expression levels into units of an integer number of plasmids per droplet added [Nishimura, K. et al., "Cell-free protein synthesis inside giant unilamellar vesicles analyzed by flow cytometry", Langmuir 28, 8426-32 (2012)]. This can be achieved in several different ways, with the choice of encapsulation method depending on the intended application of the synell.

Phospholipid liposomes are most commonly used to encapsulate synell transcription-translation systems. The technique does not require elaborate instrumentation or time consuming protocols. Typically, mixtures of diacyl phosphocholines, usually POPC (1-palmitoyl-2-oleoyl-sn-glycero-3-phosphocholine) are used, often mixed with cholesterol (to decrease the permeability of the membranes and improve folding and insertion of membrane proteins) [Mansy, S. S. & Szostak, J. W., "Thermostability of model protocell membranes", Proc. Natl. Acad. Sci. U.S.A. 105, 13351-13355 (2008); Adamala, K. & Szostak, J. W., "Non-enzymatic Template-Directed RNA Synthesis Inside Model Protocells", Science (80-.). 342, 1098-1100 (2013)]. Encapsulated within phospholipid liposomes, the synells can be exposed and operated in a variety of conditions unsuitable for top-down minimal cell chassis and foreign to any of the original organisms whose sequences inspired the synthetic components of the transcription-translation system or whose lysates are used directly. Unencapsulated molecules can be removed by dialysis or size exclusion chromatography, and the synells then transferred to a different solution in order to, for example, interface with live cells, interface with electronics, or serve as biosensors.

In example cases when synells are built for the purpose of studying the origin of life and earliest biological processes, they are often encapsulated within fatty acids, such as, but not limited to, oleic or myristoleic acid. Those membranes are less stable and are often incompatible with the divalent cation levels necessary for activity of modern biological enzymes; however, unmodified fatty acids are the most prebiotically plausible lipids to be possibly present on the early Earth and elsewhere with Earth-type life [Adamala, K. et al., "Open questions in origin of life: experimental studies on the origin of nucleic acids and proteins with specific and functional sequences by a chemical synthetic biology approach", Comput. Struct. Biotechnol. J. 9, e201402004 (2014); Peters, R. J. R. W. et al, "Cascade reactions in multicompartmentalized polymersomes", Angew. Chemie-Int. Ed. 53, 146-150 (2014); Chiu, H.-C., Lin, Y.-W., Huang, Y.-F., Chuang, C.-K. & Chern, C.-S, "Polymer Vesicles Containing Small Vesicles within Interior Aqueous Compartments and pH-Responsive Transmembrane Channels", Angew. Chemie 120, 1901-1904 (2008); Aumiller, W. M. & Keating, C. D., "Phosphorylation-mediated RNA/peptide complex coacervation as a model for intracellular liquid organelles", Nat. Chem. 8, 129-137 (2015)].

Synells do not have to be built with a single, unilamellar lipid bilayer, with all reactions happening in the lumen. Synells according to the invention may optionally contain multicompartmentalized liposomes for separating different reaction environments and performing multi-step reactions [Courtois, F. et al., "An integrated device for monitoring time-dependent in vitro expression from single genes in picolitre droplets", ChemBioChem 9, 439-446 (2008)], possibly with internal channels facilitating communications between compartments [Sunami, T. et al., "Femtoliter compartment in liposomes for in vitro selection of proteins", Anal. Biochem. 357, 128-136 (2006)], thereby mimicking the existence of separate organelles in synells [Schwarz-Schilling, M., Aufinger, L., Mückl, a. & Simmel, F. C., "Chemical communication between bacteria and cell-free gene expression systems within linear chains of emulsion droplets", Integr. Biol. (2016)].

In some embodiments, microfluidic droplets are employed for compartmentalization of synells. The microdroplets separate the content of different synells and permit parallel, high-throughput analysis of reactions [Weitz, M. et al., "Diversity in the Dynamical Behaviour of a Compartmentalized Programmable Biochemical Oscillator", Nat. Chem. 6, 295-302 (2014); Karzbrun, E., Tayar, A. M., Noireaux, V. & Bar-Ziv, R. H., "Synthetic biology. Programmable on-chip DNA compartments as artificial cells", Science 345, 829-32 (2014)]. The lack of bilayer membrane could be a drawback for certain applications, especially where membrane-bound proteins or signaling cascades are needed. Microfluidic systems permit high-throughput single cell level analysis, such as, for example, studying chemical signaling between synthetic and natural cells [Yang, Y. et al., "Self-assembly of size-controlled liposomes on DNA nanotemplates", Nat. Chem. 1-8 (2016)] or biochemical oscillators [Gudlur, S. et al.' "Peptide Nanovesicles Formed by the Self-Assembly of Branched Amphiphilic Peptides", PLoS One 7, (2012)].

Other compounds, such as, but not limited to, DNA compartments [Zhang, S. et al., "Mimicking biological membranes with programmable glycan ligands self-assembled from amphiphilic Janus glycodendrimers", Angew. Chemie-Int. Ed. 53, 10899-10903 (2014)], DNA-templated liposomes [Frankel, E. a., Bevilacqua, P. C. & Keating, C. D., "Polyamine/Nucleotide Coacervates Provide Strong Compartmentalization of Mg 2+, Nucleotides, and RNA", Langmuir 32, 2041-2049 (2016)], branched amphiphilic peptides [Brea, R. J., Hardy, M. D. & Devaraj, N. K., "Towards Self-Assembled Hybrid Artificial Cells: Novel Bottom-Up Approaches to Functional Synthetic Membranes", Chem.-A Eur. J. n/a-n/a (2015)], sugar glycodendrimersomes [Kumar, G. & Chernaya, G., "Cell-free protein synthesis using multiply-primed rolling circle amplification products", Biotechniques 47, 637-639 (2009)], and polyelectrolyte coacervates [Shin, J., Jardine, P. & Noireaux, V., "Genome replication, synthesis, and assembly of the bacteriophage T7 in a single cell-Free reaction", ACS Synth. Biol. 1, 408-413 (2012)] can also be used to build compartments, increasing complexity. Work in this area is one of the fastest progressing areas of development within synell technology [Lentini, R. et al., "Integrating artificial with natural cells to translate chemical messages that direct E. coli behavior", Nat. Commun. 5, 4012 (2014)].

Information Processing and Other Synell Functions

It is possible to couple the protein synthesis to replication of DNA in cell-free protein expression system, using multiple-primed rolling circle amplification [Takahashi, M. K. et al., "Characterizing and prototyping genetic networks with cell-free transcription-translation reactions", Methods (2015)]. While the entire replicable bacteriophage was expressed in a cell-free system [Takahashi, M. K. et al., "Rapidly Characterizing the Fast Dynamics of RNA Genetic Circuitry with Cell-Free Transcription-Translation (TX-TL) Systems", ACS Synth. Biol. 4, 503-515 (2015)], it remains unknown whether the phage can be expressed and bud out of a liposomal encapsulated synell. Control of expression of genes inside synells can be achieved via small-molecule activation of RNA aptamers [Karig, D. K., Iyer, S., Simpson, M. L. & Doktycz, M. J., "Expression optimization and synthetic gene networks in cell-free systems", Nucleic Acids Res. 40, 3763-3774 (2012)], or via cell-free genetic circuits [Noireaux, V., Bar-Ziv, R. & Libchaber, A., "Principles of cell-free genetic circuit assembly", Proc. Natl. Acad. Sci. U.S.A. 100, 12672-12677 (2003); DeVries, J. K. & Zubay, G., "DNA-directed peptide synthesis. II. The synthesis of the alpha-fragment of the enzyme beta-galactosidase", Proc. Natl. Acad. Sci. U.S.A. 57, 1010-2 (1967); Zhang, L. Y., Chang, S. H. & Wang, J., "How to make a minimal genome for synthetic minimal cell", Protein Cell 1, 427-434 (2010); Nevin, D. E. & Pratt, J., "A coupled in vitro transcription-translation system for the exclusive synthesis of polypeptides expressed from the T7 promoter", 291, 259-263 (1991)] or operons [Yadavalli, R. & Sam-Yellowe, T., "HeLa Based Cell Free Expression Systems for Expression of Plasmodium Rhoptry Proteins", J. Vis. Exp. 2015, e52772 (2015)].

In an example implementation, a set of genes inserted in a synell includes DNA replication, transcription, translation, membrane proteins, lipid compounds, and division mechanism [Brodel, A. K. et al., "IRES-mediated translation of membrane proteins and glycoproteins in eukaryotic cell-free systems", PLoS One 8, (2013)]. This represents the minimum for a fully autonomous, replicating synell, thus providing a closer analogue to the "top-down" minimal cell and wild-type cells. This presents a significant simplification since, being "bottom-up", a synell only requires that all the proteins necessary for the functions of the cell are present—either already in the cell-free transcription-translation extract used, or from introduced DNA templates.

To express genes from a DNA template, transcription and translation must happen, concurrently or sequentially. In many cell-free protein expression experiments, a so-called linked system is used: the DNA template is transcribed in a separate reaction and then RNA is transferred into the translation reaction. In example synells, mimicking many bulk transcription-translation in vitro reactions, a coupled system may be used wherein the transcription and translation happen in the same reaction mix (in the same tube for in vitro systems, or in the same compartment of a synell) [Dignam J D, Lebovitz R M, R. R., Dignam, J. D., Lebovitz, R. M., Roeder, R. G. & Dignam J D, Lebovitz R M, R. R., "Accurate transcription initiation by RNA polymerase II in a soluble extract from isolated mammalian nuclei", Nucleic Acids Res. 1, 1475-1489 (1983)].

In example instances of synells using the mammalian-derived cell-free protein synthesis system, translation may be initiated from the artificial internal ribosomal entry sites (IRES) [Caspi, Y. & Dekker, C., "Divided we stand: splitting synthetic cells for their proliferation", Syst. Synth. Biol. 249-269 (2014); Del Bianco, C. & Mansy, S. S., "Nonreplicating protocells", Acc. Chem. Res. 45, 2125-2130 (2012)]. In natural cells, mammalian translation is typically initiated from mRNA caps—a result of mRNA maturation in the nucleus. For mammalian transcription-translation systems, expression relies on T7 RNA polymerase transcription [Brödel, A. K. & Kubick, S., "Developing cell-free protein synthesis systems: a focus on mammalian cells", Pharm. Bioprocess. 2, 339-348 (2014)], and in the absence of proper mRNA maturation the transcript needs to contain IRES in order to initiate translation. One of the most commonly used mammalian cell-free protein synthesis systems is an extract from cells that have naturally lost nucleus—rabbit reticulocytes. The cell-free extracts of other mammalian cells, for example HeLa cells, are transcriptionally active [Zhu, T. F., Adamala, K., Zhang, N. & Szostak, J. W., "Photochemically driven redox chemistry induces protocell membrane pearling and division", Proc. Natl. Acad. Sci. 109, 9828-9832 (2012); Miller, D. & Gulbis, J., "Engineering Protocells: Prospects for Self-Assembly and Nanoscale Production-Lines", Life 5, 1019-1053 (2015)]. One example implementation of synell technology builds a coupled all-mammalian cell-free transcription-translation system.

Several mechanisms have been shown for controlled division of synells [Rosenblum, G. & Cooperman, B. S., "Engine out of the chassis: Cell-free protein synthesis and its uses", FEBS Lett. 588, 261-268 (2014); Dudley, Q. M., Karim, A. S. & Jewett, M. C., "Cell-free metabolic engineering: Biomanufacturing beyond the cell", Biotechnol. J. 10, 69-82 (2015); Saïda, F., Uzan, M., Odaert, B. & Bontems, F., "Expression of highly toxic genes in E. coli: special strategies and genetic tools", Curr. Protein Pept. Sci. 7, 47-56 (2006)]. Division is one of the most important functions of natural cells. Consensus in the field is currently that, for practical purposes, whether autonomous division is happening or not is a key distinction between living cells and synells.

Biosynthesis

Example implementations of synell technology are development of novel applications in biotechnology and use as basic science research tools. Synells have been widely used for biosynthesis and building bio-orthogonal biosensors. Recent developments in synell technology have permitted additional novel applications, including building chemical interfaces with natural cells and developing living technologies, as well as basic science applications such as rapid prototyping of biological circuits.

Examples of types of applications of synell technologies include, but are not limited to, the following: a) Biosynthesis of small molecules and proteins, often toxic to the living cells; also, introducing modifications like unnatural amino acids or isotope labels; b) Rapid prototyping of biology: reducing biological systems to first principles, studying biological processes in separation from interfering pathways; c) Non-invasive interface with biology: adding a bio-orthogonal layer of actuators and sensors between natural cells and environmental control signals; d) Living technologies: creating biologically inspired technologies, and bio-compatible ways of interacting between cells and electronics; and e) Biosensors: detecting molecules in the environment, using bio-degradable probes.

Example implementations of synell technology include small molecule production. In this mode, synells are used as bioreactors, for enzymatically catalyzed synthesis of biomolecules. Spatially separating elements of metabolic pathways can be very important for rapid prototyping of novel pathways, as it allows reducing the metabolic engineering to the problem of separate, yet cooperating, building blocks of different chemical transitions [Stech, M. et al., "Production of functional antibody fragments in a vesicle-based eukaryotic cell-free translation system", J Biotechnol 164, 220-231 (2012)]. Cell-free protein synthesis in synell requires shorter preparation time (from gene to expressed protein) than traditional in-vivo protein expression [Alexandrov, K. & Johnston, W. A., "Cell-Free Protein Synthesis Methods and Protocols" (2014)]. Thus, synells in biomanufacturing make fast, iterative optimization of biosynthetic pathways practical [Terada, T. & Yokoyama, S., "*Escherichia coli* Cell-Free Protein Synthesis and Isotope Labeling of Mammalian Proteins", Methods in Enzymology 565 (Elsevier Inc., 2015)].

Bulk cell-free protein synthesis has been extensively used to express toxic gene products, i.e. proteins that are toxic to the live hosts [Vinarov, D. a., Newman, C. L. L. & Markley, J. L., "Wheat germ cell-free platform for eukaryotic protein production", FEBS J. 273, 4160-4169 (2006)] but would not harm synells. Implementations of synells creating functional antibodies utilize the rapid turnover and the synells' small volumes, ease of reproduction in ensembles, and freedom of design, including mixtures of subtypes of synells, to cut costs and iterative optimization time when creating protein fragments that would typically otherwise require expression in a live animal [Des Soye, B. J., Patel, J. R., Isaacs, F. J. & Jewett, M. C., "Repurposing the translation apparatus for synthetic biology", Curr. Opin. Chem. Biol. 28, 83-90 (2015)].

Various example implementations of synell-based protein synthesis include expressed proteins containing modified amino acids such as selenomethionine for crystallization [Hong, S. H., Kwon, Y.-C. & Jewett, M. C., "Non-standard amino acid incorporation into proteins using *Escherichia coli* cell-free protein synthesis", Front. Chem. 2, 34 (2014)], isotope labelling for NMR and kinetic analysis [Li, J. et al., "Cell-free protein synthesis enables high yielding synthesis of an active multicopper oxidase", Biotechnol. J. 212-218 (2015); Carlson, E. D., Gan, R., Hodgman, C. E. & Jewett, M. C., "Cell-free protein synthesis: Applications come of age", Biotechnol. Adv. 30, 1185-1194 (2012)], and expanding the codon alphabet beyond the natural amino acids [Hillebrecht, J. R. & Chong, S., "A comparative study of protein synthesis in in vitro systems: from the prokaryotic reconstituted to the eukaryotic extract-based", BMC Biotechnol. 8, 58 (2008); Kwon, Y.-C. & Jewett, M. C., "High-throughput preparation methods of crude extract for robust cell-free protein synthesis", Sci. Rep. 5, 8663 (2015); Spirin, A. S., "High-throughput cell-free systems for synthesis of functionally active proteins", Trends Biotechnol. 22, 538-545 (2004)]. A synell system used to express copper-coordinating oxidases provides an advantage over functional assemblies in live systems [Gagoski, D. et al., "Gateway-compatible vectors for high-throughput protein expression in pro- and eukaryotic cell-free systems", J. Biotechnol. 195, 1-7 (2015)].

The costs of preparation and performing cell-free reactions in bulk, and even more so in synells, have decreased to the point of becoming industrially viable [Kuruma, Y. & Ueda, T., "The PURE system for the cell-free synthesis of membrane proteins", Nat. Protoc. 10, 1328-1344 (2015)]. Cell-free protein synthesis techniques are high-throughput [Mikami, S., Kobayashi, T., Masutani, M., Yokoyama, S. & Imataka, H., "A human cell-derived in vitro coupled transcription/translation system optimized for production of recombinant proteins", Protein Expr. Purif. 62, 190-198 (2008); Fenz, S. F., Sachse, R., Schmidt, T. & Kubick, S., "Cell-free synthesis of membrane proteins: Tailored cell models out of microsomes", Biochim. Biophys. Acta-Biomembr. 1838, 1382-1388 (2014); Sachse, R., Dondapati, S. K., Fenz, S. F., Schmidt, T. & Kubick, S., "Membrane protein synthesis in cell-free systems: From bio-mimetic systems to bio-membranes", FEBS Lett. 588, 2774-2781 (2014)], and producing clones of genes of interest in cell-free expression vectors is compatible with the widely used Gateway cloning technique, giving access to many libraries of ORF's and functional proteins [Hein, C., Henrich, E., Orbán, E., Dötsch, V. & Bernhard, F., "Hydrophobic supplements in cell-free systems: Designing artificial environments for membrane proteins", Eng. Life Sci. 14, 365-379 (2014)]. The same technology ported to synells offers additional cost and time savings.

In one embodiment, synells with a phospholipid membrane are used for the production of membrane-associated proteins, orthogonal and complementary not only to live expression systems, but also to classical tube reaction cell-free protein synthesis. Proteins that need a bilayer membrane for correct folding and activity have been notoriously difficult to express and purify in vivo, and cell-free systems have proven a very valuable tool for expression of such products [Katzen, F., Peterson, T. C. & Kudlicki, W., "Membrane protein expression: no cells required", Trends Biotechnol. 27, 455-460 (2009); Henrich, E., Hein, C., Deutsch, V. & Bernhard, F., "Membrane protein production in *Escherichia coli* cell-free lysates", FEBS Lett. 589, 1713-1722 (2015); Schwarz, D. et al., "Preparative scale expression of membrane proteins in *Escherichia coli*-based continuous exchange cell-free systems", Nat. Protoc. 2, 2945-2957 (2007); Kalmbach, R. et al., "Functional Cell-free Synthesis of a Seven Helix Membrane Protein: In situ Insertion of Bacteriorhodopsin into Liposomes", J. Mol. Biol. 371, 639-648 (2007); Ishihara, G. et al., "Expression of G protein coupled receptors in a cell-free translational system using detergents and thioredoxin-fusion vectors", Protein Expr. Purif. 41, 27-37 (2005)]. Membrane proteins can be expressed directly in synells or in conjunction with micelles, liposomes, or detergents, providing high level of control over expression conditions and allowing easy choice of purification methods [Corin, K., Cook, B. & Zhang, S., "A Robust, Rapid, and Simple Method of Producing Olfactory Receptors Using Commercial *E. coli* Cell-Free Systems", Olfactory Recept. Methods Protoc. 1003, 229-238 (2013)]. Membrane proteins can be synthetized in PURE [Katzen, F., Peterson, T. C. & Kudlicki, W., "Membrane protein expression: no cells required", Trends Biotechnol. 27, 455-460 (2009)], bacterial [Oza, J. P. et al., "Robust production of recombinant phosphoproteins using cell-free protein synthesis", Nat. Commun. 6, 8168 (2015)], or in eukaryotic systems [Des Soye, B. J., Patel, J. R., Isaacs, F. J. & Jewett, M. C., "Repurposing the translation apparatus for synthetic biology", Curr. Opin. Chem. Biol. 28, 83-90 (2015)], with synells providing a versatile platform for optimization of expression conditions and purification. In some embodiments, membrane proteins are expressed continuously in preparative scale, similarly to what has been demonstrated in bulk cell-free expression [Knapp, K. G., Goerke, A. R. & Swartz, J. R., "Cell-free synthesis of proteins that require disulfide bonds using glucose as an energy source", Biotechnol. Bioeng. 97, 901-908 (2007)], functional channelrhodopsins [Maeda, Y. T. et al., "Assembly of MreB filaments on liposome membranes: A synthetic biology approach", ACS Synth. Biol. 1, 53-59 (2012)], GPCR [Westhorpe, F. G., Fuller, C. J. & Straight, A. F., "A cell-free CENP-A assembly system defines the chromatin requirements for centromere maintenance", J. Cell Biol. 209, 789-801 (2015); Kim, E. Y. & Tullman-Ercek, D., "Engineering nanoscale protein compartments for synthetic organelles", Curr. Opin. Biotechnol. 24, 627-632 (2013)], and olfactory receptors [Hodgman, C. E. & Jewett, M. C., "Cell-free synthetic biology: Thinking outside the cell", Metab. Eng. 14, 261-269 (2012)]. Porting these bulk in vitro systems to synells greatly expands the range of signals that may be detected by a synell, as well as provide methods of control of synell functions via light or signaling cascades.

Expression of various proteins in synells has significance beyond the preparative biosynthesis scale. The functions and properties of synells depend on the functional proteins expressed in the synell, and therefore advancements in the cell-free protein synthesis expand the repertoire of applications of synell technology in parallel.

Rapid Prototyping of Biology

Natural biological systems are inherently complex and difficult to model. Synell technologies provide a platform for assembling elements of biology in separation from the rest of the living cell, permitting study of biological systems by reducing those systems to first principles. It also provides a platform for assembling control and readout tools that can be later used in biological systems.

In some example implementations, synells are used to design and test synthetic genetic circuits, providing a platform for developing biological logic gates and nucleic acid control systems, as well as for studying gene expression regulation mechanisms [Noireaux, V., Bar-Ziv, R. & Libchaber, A., "Principles of cell-free genetic circuit assembly", Proc. Natl. Acad. Sci. U.S.A. 100, 12672-12677 (2003); DeVries, J. K. & Zubay, G., "DNA-directed peptide synthesis. II. The synthesis of the alpha-fragment of the enzyme beta-galactosidase", Proc. Natl. Acad. Sci. U.S.A. 57, 1010-2 (1967); Zhang, L. Y., Chang, S. H. & Wang, J., "How to make a minimal genome for synthetic minimal cell", Protein Cell 1, 427-434 (2010); Nevin, D. E. & Pratt, J., "A coupled in vitro transcription-translation system for the exclusive synthesis of polypeptides expressed from the T7 promoter", 291, 259-263 (1991)]. They provide a model to study protein production, post-translational modifications (phosphorylation [Kita, H. et al., "Replication of genetic information with self-encoded replicase in liposomes", ChemBioChem 9, 2403-2410 (2008)], disulfide bonds [Tsuji, G., Fujii, S., Sunami, T. & Yomo, T., "Sustainable proliferation of liposomes compatible with inner RNA replication", Proc. Natl. Acad. Sci. 201516893 (2015)], glycosidation [Machida, K., Masutan, M. & Imataka, H., "Protein Synthesis in vitro: Cell-Free Systems Derived from Human Cells" (2012); Del Bianco, C. & Mansy, S. S., "Nonreplicating protocells", Acc. Chem. Res. 45, 2125-2130 (2012)]), to model cellular structures (for example MreB [Adamala, K., Engelhart, A. E. & Szostak, J. W., "Generation of Functional RNAs from Inactive Oligonucleotide Complexes by Non-enzymatic Primer Extension", J. Am. Chem. Soc. 137, 483-489 (2015)]), to study chromatin dynamics (for example, using *Xenopus* egg extract [Engelhart, A. E., Adamala, K. P. & Szostak, J. W., "A simple physical mechanism enables homeostasis in primitive cells", Nat. Chem. 1-6 (2016)]), and to model whole organelles [Adamala, K. & Szostak, J. W., "Competition between model protocells driven by an encapsulated catalyst," Nat. Chem. 5, 495-501 (2013)].

Study of Darwinian evolution is implemented by building synells exhibiting elements of Darwinian evolution allows studying the chemical basis of biological evolution [Elowitz, M. & Lim, W. a., "Build life to understand it", Nature 468, 889-890 (2010); Adamala, K., Engelhart, A. E. & Szostak, J. W., "Collaboration between primitive cell membranes and soluble catalysts", Nat. Commun. 7, 1-7 (2016)]. Synell models exist for replication [Szostak, J. W., Bartel, D. P. & Luisi, P. L., "Synthesizing Life", Nature 409, 387-390 (2001); Hansen, M. M. K. et al., "Macromolecular crowding creates heterogeneous environments of gene expression in picolitre droplets", Nat. Nanotechnol. 1-8 (2015); Fritz, B. R., Jamil, O. K. & Jewett, M. C., "Implications of macromolecular crowding and reducing conditions for in vitro ribosome construction", Nucleic Acids Res. 43, 4774-4784 (2015)], protein selection [Karzbrun, E., Tayar, A. M., Noireaux, V. & Bar-Ziv, R. H., "Synthetic biology. Programmable on-chip DNA compartments as artificial cells", Science 345, 829-32 (2014)], homeostasis [Tan, C., Saurabh, S., Bruchez, M. P., Schwartz, R. & Leduc, P., "Molecular crowding shapes gene expression in synthetic cellular nanosystems", Nat. Nanotechnol. 8, 602-8 (2013)], and the mechanism for internal catalysts impairing fitness on the cell population [Roca, X. & Karginov, F. V., "RNA biology in a test tube—an overview of in vitro systems/assays", Wiley Interdiscip. Rev. RNA 3, 509-527 (2012); Sawasaki, T., Ogasawara, T., Morishita, R. & Endo, Y., "A cell-free protein synthesis system for high-throughput proteomics", Proc. Natl. Acad. Sci. U.S.A. 99, 14652-7 (2002)]. This reductionist approach to biology is also crucial in the studies of the origin of biological life. Building synells from the simple, prebiotically plausible chemicals, not only gives insights into the probable routes of the origin of life on Earth, but also helps defining physicochemical and geochemical boundaries of life [Chiu, H.-C., Lin, Y.-W., Huang, Y.-F., Chuang, C.-K. & Chern, C.-S, "Polymer Vesicles Containing Small Vesicles within Interior Aqueous Compartments and pH-Responsive Transmembrane Channels", Angew. Chemie 120, 1901-1904 (2008); Sawasaki, T. et al., "Genome-scale, biochemical annotation method based on the wheat germ cell-free protein synthesis system", Phytochemistry 65, 1549-1555 (2004)].

Molecular crowding is one of the essential aspects of biology that cannot be practically studied in vivo, as it is impossible to significantly change the osmolality of live cells. In contrast, the synell system allows adjusting of many parameters, including osmolality of the solution, thus allowing studies of molecular crowding on biological reactions, most notably all elements of gene expression, including ribosome formation [Lee, K. H. & Kim, D. M., "Applications of cell-free protein synthesis in synthetic biology: Interfacing bio-machinery with synthetic environments", Biotechnol. J. 8, 1292-1300 (2013); Jewett, M. C. & Noireaux, V., "Synthetic biology: Tailor-made genetic codes", Nat. Chem. 8, 291-292 (2016); Sawasaki, T. et al., "A bilayer cell-free protein synthesis system for high-throughput screening of gene products", FEBS Lett 514, 102-105 (2002)]. Another difficult to disturb aspect of live systems that can be extensively studied in a synell system is RNA biology, including RNA maturation and small RNA regulatory pathways [Santos-Aberturas, J., Don, M., Waldo, G. S. & Bornscheuer, U. T., "In-depth high-throughput screening of protein engineering libraries by split-GFP direct crude cell extract data normalization", Chem. Biol. 22, 1406-1414 (2015)].

Recent advancements in high-throughput proteomic [Georgi, V. et al., "On-chip automation of cell-free protein synthesis: new opportunities due to a novel reaction mode", Lab Chip 16, 269-81 (2016)] and identifying open reading frames in cDNA libraries [Sundaresh, S. et al., "Identification of humoral immune responses in protein microarrays using DNA microarray data analysis techniques", Bioinformatics 22, 1760-1766 (2006)] are also possible with the use of cell-free systems. The synthetic of proteins in cell-free system can also be integrated with downstream analysis, providing a high-throughput tool for studying function of novel proteins [Yadavalli, R., Ledger, C. & Sam-Yellowe, T. Y., "In vitro human cell-free expression system for synthesis of malaria proteins", Parasitol. Res. 111, 2461-2465 (2012]. The "custom genetic codes" [Tsuboi, T. et al., "Wheat germ cell-free system-based production of malaria proteins for discovery of novel vaccine candidates", Infect. Immun. 76, 1702-1708 (2008)] give access to novel functions of proteins, using unnatural amino acid residues to improve protease stability and to explore chemical properties of peptides beyond the naturally available functionalities of standard amino acids [Hillebrecht, J. R. & Chong, S., "A comparative study of protein synthesis in in vitro systems: from the prokaryotic reconstituted to the eukaryotic extract-based", BMC Biotechnol. 8, 58 (2008)]. Other protein function studies that are possible due the application of synells include screening for targets of kinases and proteinases [Fernandez-Robledo, J. A. & Vasta, G. R., "Production of recombinant proteins from protozoan parasites", Trends Parasitol. 26, 244-254 (2016)] or screening for novel mutant proteins [Franco, D. et al., "Stimulation of poliovirus RNA synthesis and virus maturation in a HeLa cell-free in vitro translation-RNA replication system by viral protein 3CDpro", Virol. J. 2, 86 (2005)].

Another example application of synell technology is the study of particular biological processes by building models of diseases. For example, synells may take the place of in vitro bulk cell-free protein systems that have already been used to study malaria parasite cell cycle (in bacteria [Molla, A., Paul, A. V & Wimmer, E., "Cell-free, de novo synthesis of poliovirus", Science (80-.) 1184, 1647-51 (1991)], mammalian [Caspi, Y. & Dekker, C., "Divided we stand: splitting synthetic cells for their proliferation", Syst. Synth. Biol. 249-269 (2014); Brakstad, O. G., Throne-Holst, M., Netzer, R., Stoeckel, D. M. & Atlas, R. M., "Microbial communities related to biodegradation of dispersed Macondo oil at low seawater temperature with Norwegian coastal seawater", Microb. Biotechnol. 8, 989-998 (2015)], wheat germ [Bedau, M. A., McCaskill, J. S., Packard, N. H., Parke, E. C. & Rasmussen, S. R., "Introduction to Recent Developments in Living Technology", Artif. Life 298, 291-298 (2013)] and rabbit reticoulate [Bedau, M. a, McCaskill, J. S., Packard, N. H. & Rasmussen, S., "Living technology: exploiting life's principles in technology", Artif. Life 16, 89-97 (2010)] systems), to look for Ebola markers [Endoh, T. et al., "Cell-free protein synthesis at high temperatures using the lysate of a hyperthermophile", J. Biotechnol. 126, 186-195 (2006)], or to study poliovirus (in HeLa extract [Rampioni, G. et al., "Chemical communication between synthetic and natural cells: a possible experimental design", Electron. Proc. Theor. Comput. Sci. 130, 14-26 (2013); Stano, P. et al., "Semi-synthetic minimal cells as a tool for biochemical ICT", BioSystems 109, 24-34 (2012)]).

Non-Invasive Interface with Biology

It has been recently shown that synells can be used to communicate with natural cells [Karig, D. K., Iyer, S., Simpson, M. L. & Doktycz, M. J., "Expression optimization and synthetic gene networks in cell-free systems", Nucleic Acids Res. 40, 3763-3774 (2012)]. In an example implementation, synells control living cells in the cellular environment without the need to modify the natural cells. This application of synell technology provides a novel practical readout of cell states, amounting to a suite of non-invasive sensors in living organisms, as well as providing mechanisms for the control of living cells. As an example, for the "oil-eating" bacteria [Rogers, J. K. et al., "Synthetic biosensors for precise gene control and real-time monitoring of metabolites", Nucleic Acids Res. gkv616 (2015)] currently used for biodegradation of oils spills, synells may be employed to replace living cells carrying the same function, therefore overcoming reservations against releasing genetically modified organisms into the wild.

A particular embodiment involving co-locating synells and natural cells elucidates the mechanisms of small-molecule mediated cell functions, similar to the case of quorum sensing bacteria [Yang, Y. et al., "Self-assembly of size-controlled liposomes on DNA nanotemplates", Nat. Chem. 1-8 (2016)].

Synells for Hybrid Technologies

Synells implemented as computation devices, either independently or on an interface with natural cells and machines [Vamvakaki, V. & Chaniotakis, N. a., "Pesticide detection with a liposome-based nano-biosensor", Biosens. Bioelectron. 22, 2848-53 (2007)], make practical the interface between biology and technology, because synells combine the bio-orthogonality advantage of biological computing with the programmability of traditional computing devices [Kobori, S., Ichihashi, N., Kazuta, Y. & Yomo, T., "A controllable gene expression system in liposomes that includes a positive feedback loop.", Mol. Biosyst. 9, 1282-5 (2013)].

Synells acting as transducers of chemical communication signals between electronic and optical circuitry and natural, transgenic, or minimal living cell chassis facilitate development of biological computing systems [Jin, H. J. et al., "Nanovesicle-based bioelectronic nose platform mimicking human olfactory signal transduction", Biosens. Bioelectron. 35, 335-341 (2012)], since synells play both roles of interface between natural cells and external inorganic sensors and actuators, as well as being information processing units themselves [Lee, S. H. et al., "Mimicking the human smell sensing mechanism with an artificial nose platform", Biomaterials 33, 1722-1729 (2012)], because synells process input signals such as small molecules emitted by natural cells, and chemicals, electrical signals, or light signals from experimenter. In one example embodiment, the output of such a system is fluorescent protein spectrophotometrically measured by a plate reader, nanodrop, or microscope, while in parallel, small molecule signals released by the synells are passed on for mass spectrometry analysis while also inducing potential responses from the natural cells. Synells make possible bidirectionally affecting and remotely monitoring the interactions between natural bacteria, mammalian cell co-cultures, such as, for example, nerve and immune system co-cultures in the presence of drugs, and other small molecules that either the experimenter adds or the synells produce locally [Yang, Y. et al., "Self-assembly of size-controlled liposomes on DNA nanotemplates", Nat. Chem. 1-8 (2016); Karig, D. K., Iyer, S., Simpson, M. L. & Doktycz, M. J., "Expression optimization and synthetic gene networks in cell-free systems", Nucleic Acids Res. 40, 3763-3774 (2012)]. In this implementation, the ensemble nature of synells provide a unique capability of accumulating large statistics over small total cell sample sizes in order to detect and repeat experiments that are currently prohibitively expensive and time consuming.

Biosensors

In a preferred embodiment, synells according to the invention may be used for control and readout of biology. Synells implemented as liposome-based biosensors [Zamecnik, P. C. & Keller, E. B., "Relation between phosphate energy donors and incorporation of labeled amino acids into proteins", J. Biol. Chem. 209, 337-354 (1954; Marshall W. Nirenberg, J. H. M., "The dependence of cell-free protein synthesis in E. coli upon naturally occurring or synthetic polyribonucleotides", PNAS 47, 1588-1602 (1961)] use proteins to detect the analyte and are fully biodegradable and biorthogonal. Synells providing precise control over the detection reaction and protein synthesis have been reduced to practice [Zamecnik, P. C. & Keller, E. B., "Relation between phosphate energy donors and incorporation of labeled amino acids into proteins", J. Biol. Chem. 209, 337-354 (1954].

Synells introduce a level of genetic circuit computation into the sensing or actuating system: since the signal is contingent on protein expression and/or enzymatic activity, it is possible to introduce fine control of the signal for the actuators as well as single amplification and precise location for the sensors. Natural cells can be controlled by variety of small molecules. Using synells as a layer of processing between the environmental sources and the cells expands the repertoire of chemical signals that can effectively trigger responses from unmodified cells, but also localize the response, since actuator synells can be precisely localized.

The environmental trigger molecule does not induce response of natural cells, but instead it triggers release or production of a cell-specific control molecule from synells.

Figures 3, 4:
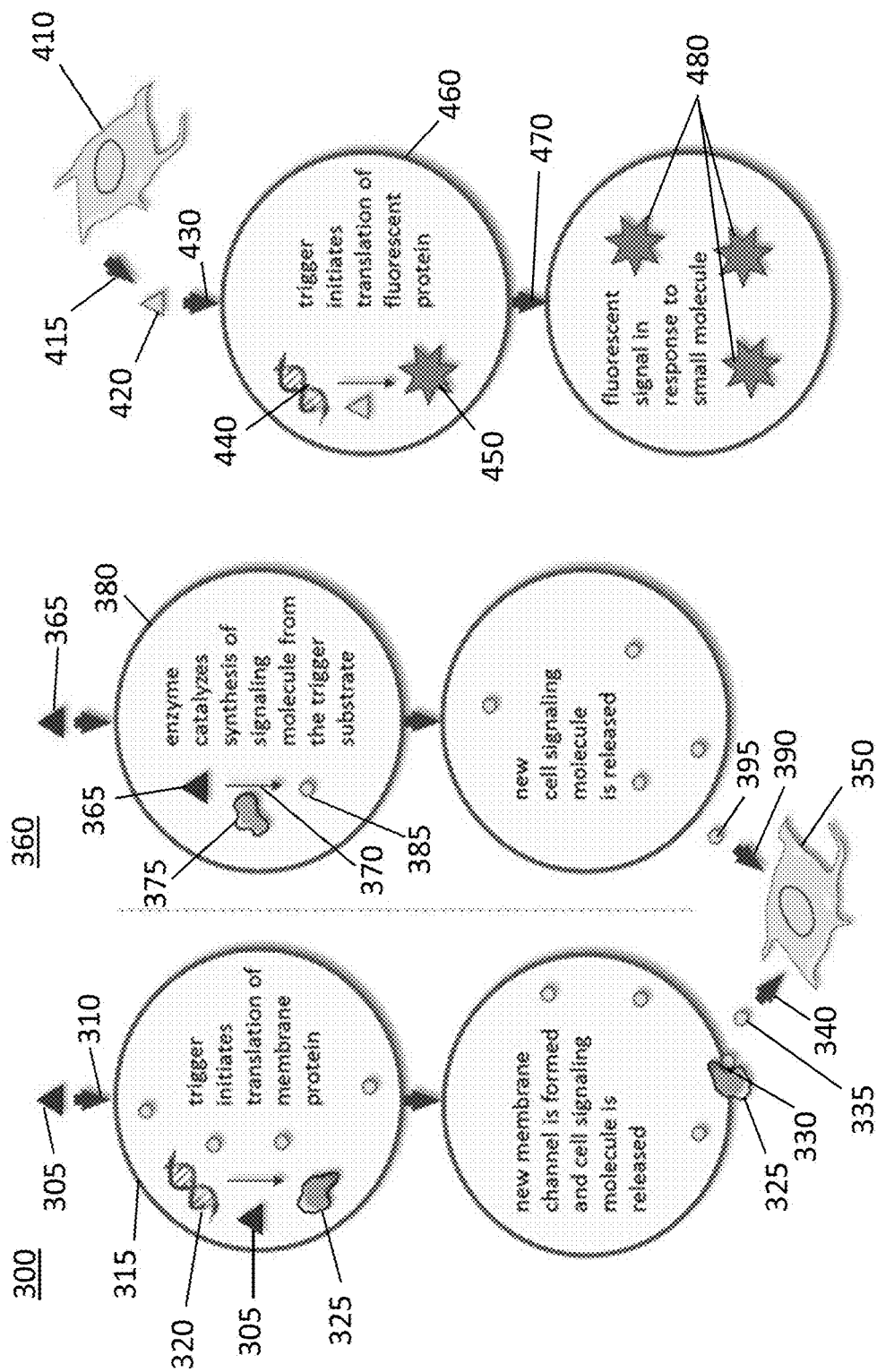
FIG. 3 depicts two example embodiments of pathways using synells for control of cells, according to one aspect of the invention.
FIG. 4 depicts an example implementation of a basic biosensor synell that detects signals from cells, according to one aspect of the invention.

FIG. 3 depicts two example embodiments of pathways using synells for control of cells, according to one aspect of the invention. In pathway 300, trigger molecule 305 from the environment permeates 310 inside actuator synell 315, where it initiates translation 320 of membrane protein 325, inducing protein expression and resulting in the insertion of membrane pore 330 and release of cell-specific signaling molecule 335 to control 340 cell 350. This approach had recently been used to augment the sensing properties of bacteria [Karig, D. K., Iyer, S., Simpson, M. L. & Doktycz, M. J., "Expression optimization and synthetic gene networks in cell-free systems", Nucleic Acids Res. 40, 3763-3774 (2012)]. In pathway 360, environmental trigger 365 is a substrate in a reaction, catalyzed 370 by enzymes 375 inside synell 380, and the reaction product 385 is released 390 to act as a cell-specific signaling molecule 395 to control cell 350. Both designs create actuators for unmodified natural cells, using a wide variety of small molecule activators, obtaining localized and tunable response from natural cells. Sensing small molecules in the environment, or sensing metabolites from natural cells in the organism, require bio-degradable and bio-orthogonal sensors.

FIG. 4 depicts an example implementation of a basic biosensor synell that detects signals from cells, expresses fluorescent reporter protein in response to an analyte molecule. In FIG. 4, cell 410 produces 415 trigger 420 which initiates 430 translation 440 of fluorescent protein 450 within basic biosensor synell 460. Biosensor synell 460 then emits 470 fluorescent signals 480, indicating the presence of the analyte molecule.

Synells with functional gene expression machinery, and therefore the possibility to deploy multiple layers of genetic circuit regulation, represent a new type of "smart" biosensors. One example of such system includes a synell biosensor, such as the one in FIG. 4, along with a positive feedback loop used to increase signal to noise for detection of small molecule analytes [Roberts, B. E. & Patersont, B. M., "Efficient translation of tobacco mosaic virus RNA and rabbit globin 9S RNA in a cell-free system from commercial wheat germ", PNAS 70, 2330-2334 (1973)].

Synell technologies require the use of highly temperature-sensitive cell-free protein expression enzymes, which must be stored in −80° C. until ready to use. Recent advancements offer partial solution to this problem. The cell-free protein synthesis extract can be lyophilized without significant loss of activity [Anderson, M. J., Stark, J. C., Hodgman, C. E. & Jewett, M. C., "Energizing eukaryotic cell-free protein synthesis with glucose metabolism", FEBS Lett. 589, 1723-1727 (2015)]. A field paper-based cell-free protein synthesis sensor was developed for detection of Ebola virus DNA and as a glucose sensor [Endoh, T. et al., "Cell-free protein synthesis at high temperatures using the lysate of a hyperthermophile", J. Biotechnol. 126, 186-195 (2006)]. Synells may be implemented as environmental sensors and may also find applications diagnostics, especially in the new field of "personalized medicine", where detecting certain sequences in a patient's genotype directs the treatment.

Odorant detection has long been one of the most difficult challenges in biosensing. While classical analytical chemistry methods are very good at detection and identification of odorants, robust field methods based on biological olfactory systems have recently gained attention. Implementing synells to express functional olfactory receptors that have been successfully expressed in cell-free protein expression system [Hodgman, C. E. & Jewett, M. C., "Cell-free synthetic biology: Thinking outside the cell", Metab. Eng. 14, 261-269 (2012)] is directly applicable to making robust artificial noses and machine olfactors [Mclaughlin, S., "The Preparation and Characterization of a Cell-free System from Saccharomyces cereuisiae That Translates Natural Messenger Ribonucleic Acid", J Biol Chem 254, 3965-3969 (1979); Alexander S. Spirin, Vladimir I. Baranov, Lubov' A. Ryabova, Sergey Yu. Ovodov, Y. B. A., "A Continuous Cell-Free Translation System Capable of Producing Polypeptides in High Yield", Science (80-.). 242, 1162-4 (1988)].

Digital Transfer and Ensembles

The use of synells facilitates going beyond biology, as they can be inexpensively iteratively optimized in both composition and conditions. For instance, simulating conditions on Mars and examining the behavior of a vast number of different synells becomes within imminent reach via individual synell screening. Even a one-off success experiment can be detected and then identical or interactively optimized synells can be generated at will in vast numbers to concentrate on the area. This does not require a naturally occurring cell to evolve new properties to adapt to the hostile Martian environment, it simply requires the continuous generation of synells of various compositions until those that manage to thrive in the defined environment are detected.

A novel application of synells is studying biochemistry as ensembles. At the beginning of the last century, the concept of a statistical ensemble revolutionized physics and chemistry. Assembling large numbers of identically prepared synells allows the experimenter to ask and answer questions using the powerful mathematical tools of ensembles. The implications of being able to literally repeat the same experiment at different times using identically prepared ensembles of synells become clear when the differences and similarities between cell colonies versus synell ensembles are considered. A typical unicellular colony is made up of many cells of identical genotype that can be traced back to a common single ancestor parent cell. During cell division the parent cell undergoes dramatic internal and morphological changes before literally disappearing to be replaced by two daughter cells. While the genome sequence may remain exactly identical, by any physicochemical measurement, the two daughter cells at this stage are closer copies of each other than either of them is to their common parent in the moments before division. One cannot "rewind" that cell division event and study it under different conditions.

In other words, it is impractical to take a thousand single cells from a single colony and attempt to grow one thousand colonies accumulating statistics as individual cell histories matter. One cannot treat any collection of measurements on a cell as representing a "microstate" representing the states accessible to the colony as a whole. Conversely, one cannot reproduce screening-type measurement on an assembled mixture of different genotype and phenotype cells. Both of these are example applications of synell technology.

This nuance becomes important when one considers how an ensemble of identically assembled synells differs from a colony of identical-genotype dividing cells. and how an ensemble made of differently-made synells differs from a mixture of different-genotype cells. Ensembles of synells permit studying biological and biochemical processes with previously inaccessible tools of statistical analysis of discrete states and transitions.

Figures 5, 6:
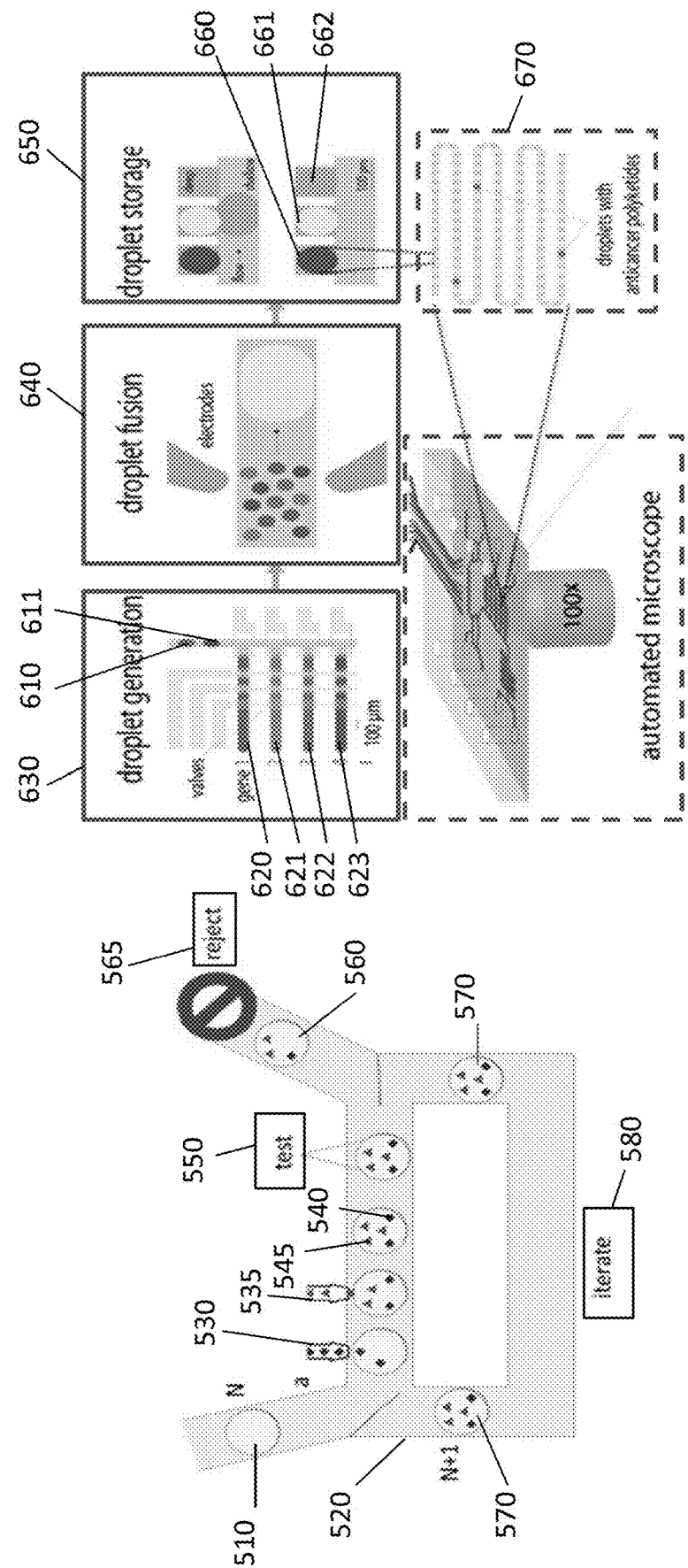
FIG. 5 depicts an example methodology for synell development via iterative design, according to one aspect of the invention.
FIG. 6 depicts an example methodology employing microfluidic chips to enable production and evaluation of ensembles of different synells interacting in mixtures of variable complexity, according to one aspect of the invention.

FIGS. 5 and 6 depict examples of methodologies for synell development and on-demand biosynthesis. FIG. 5 depicts an example methodology for synell development via iterative design, according to one aspect of the invention. As depicted in FIG. 5, ensembles of identically prepared synells may be made with precise control over type and number of genes using droplet microfluidics, assaying via flow cytometry, including during intermediate steps, and rejecting any synell that does not pass each test. This permits tuning of precision at low overhead, since the same stream of synells can be recycled past the same droplet microfluidic injector and assaying system, gradually accumulating contents. In FIG. 5, synell compartment 510 enters chamber 520 and is injected 530, 535 with synell components 540, 545. Each synell is tested 550 and failed synells 560 are rejected 565. Passing synells 570 iterate 580 within the chamber for additional cycles until the desired synell is achieved. Alternatively, a series of microfluidic droplet injectors and flow cytometer assayers can be arranged in a linear series, without iteration.

FIG. 6 depicts an example methodology for "on-demand" biosynthesis, employing microfluidic chips to enable production and evaluation of ensembles of different synells interacting in mixtures of variable complexity, including in random combinations under unusual "adaptive pressures". Synells may be created and selected based on any desired traits, including, but not limited to, multi-synell cooperation, emergence of unusual features, or statistical rarity. As depicted in FIG. 6, droplets 610, 611 containing different components 620, 621, 622, 623 are generated 630, then fused 640 and stored 650 in separate wells 660, 661, 662 of a microfluidic chip. Once a desired location on the chip is detected 670, many copies of it can be produced and statistically evaluated. The contents of each well will be replicated, since there is a record of which synells and at what ratios were mixed in each well. Combinatorial statistics can be accumulated, enabling investigation of phase spaces that traditionally would be prohibitively expensive to explore, as well as one-offs that would normally go undetected or be impossible to reproduce.

Figure 7:
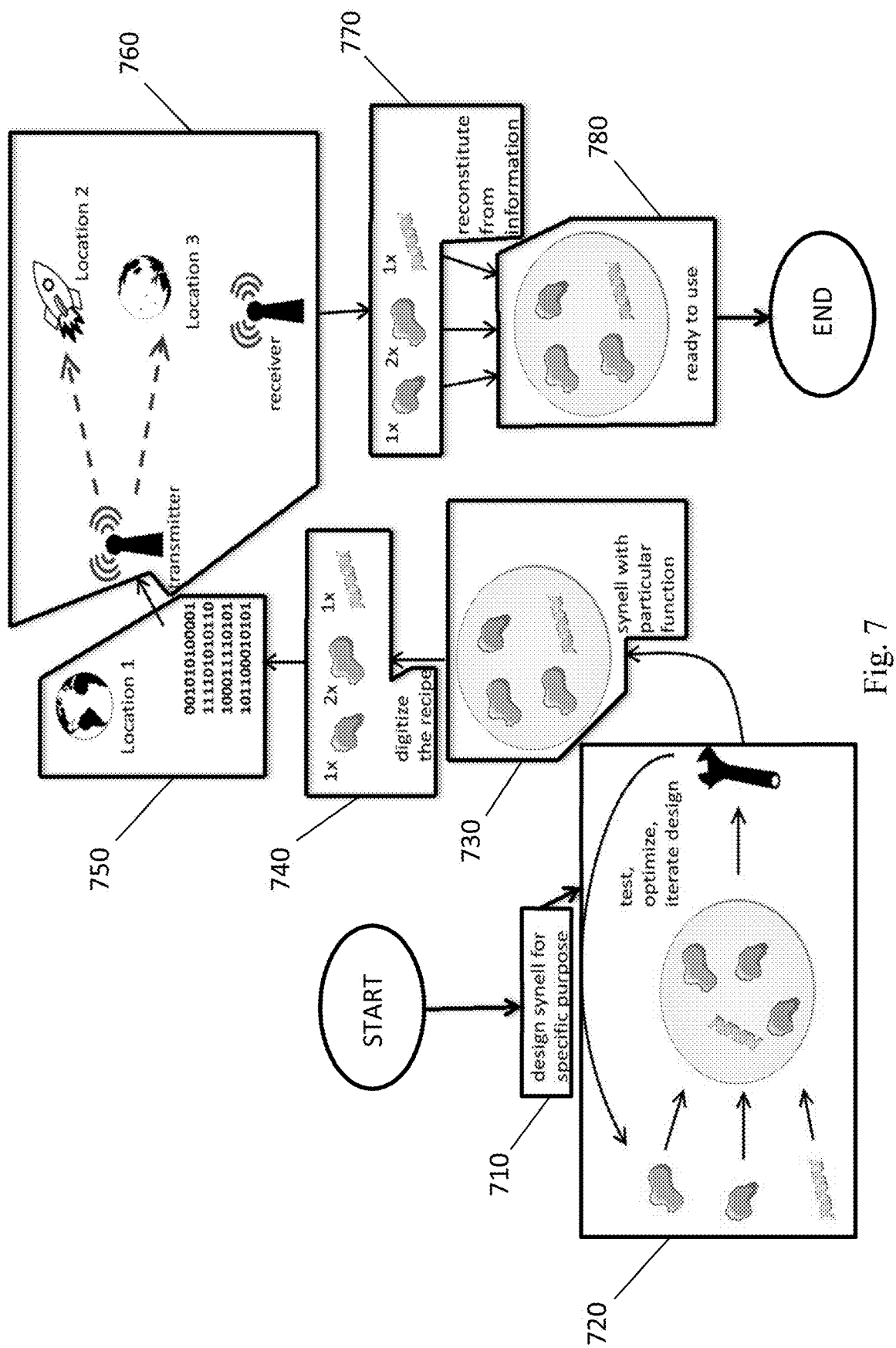
FIG. 7 illustrates an example method by which synells according to the invention can be reproduced without the constraint of local reproduction.

Synells offer a complete departure from the strongly limit imposed by biology: local reproduction. FIG. 7 illustrates an example method by which synells according to the invention can be reproduced without the constraint of local reproduction. In FIG. 7, a synell is designed 710, then tested and optimized through iteration 720 to produce 730 a synell having the desired function. The "recipe" 740 for the perfected synell is digitized 750. Optionally, the digitized recipe may be stored electronically, and then later reconstituted locally to produce additional synells having the desired function. In the embodiment of FIG. 7, the digitized recipe is transmitted 760 to one or more other locations, where it is reconstituted 770 to produce 780 additional synells having the desired function.

As shown in FIG. 7, information necessary to assemble synells of specific function discovered locally can be transmitted globally at the speed of light. To reproduce the results obtained by the sender using a complex experimental assaying system the receiver only needs a microfluidic assembler. The labor and technology-intensive task of discovering and optimizing a synell composition or mixture does not have to be done by the receiver once a set of primitive interchangeable parts and assembly machinery is distributed.

Traditionally, the information contained in the genetic material can travel only as far and as fast as the mass of the nucleic acids being duplicated during cell division. Moreover, as in the cases of seeds and frozen cells, the storage and protection schemes during transport of offspring impose inefficiencies and require complex technologies. In the case of synells, since their autonomous reproduction is unnecessary once a successful formula for a synell is discovered locally, it can be simply transmitted globally or through empty space as digital information riding on radio waves at the speed of light (and using symbology for compression makes high bit rates and practically zero error rates feasible with currently available apparatus) to anywhere with a synell-generating apparatus, be it in another lab, country, spaceship or a planet. Synells are currently the only established technology offering a single-use bioreactor whose performance and design can be built, screened, and iteratively optimized, making combinatorial scale up practical.

Specific Implementation Examples

A preferred implementation of a protocol suitable for use in a method for creating synells according to an aspect of the invention is as follows:

1. Mix lipids at the desired composition in DCM, dry overnight or under vacuum. Use total 15 mg of lipids, in glass vial.

2. Add 350 uL liquid parafin to lipid film. Flush with nitrogen (optional)

3. Incubate overnight with shaking, at 37 C. This can be stored longer (few days) with shaking.

4. Add 30 uL of the tx/tl reaction (complete with plasmid etc. to total volume of 30 uL) to the parafilm. For each reaction:

TABLE 1

|  | stock | final | 30 uL reaction |
|---|---|---|---|
| extract |  | 0.33 final volume | 10 |
| Mg-glutamate (mM) | 1000 | 12 mM | 0.36 |
| K-glutamate (mM) | 3000 | 130 mM | 1.3 |
| DTT (mM) | 100 | 1 | 0.3 |
| energy mix current energy mix Feb. 17, 2017 10x stock | 10× | 1× | 3 |
| amino acids 20 mM stock (10×) Mar. 15, 2017 |  | 2 mM | 3 |
| plasmid working stock 0.1 uM | 0.1 uM | typically 2-10 nM |  |
| water to total |  |  | to total 30 uL |

5. Vortex paraffin with tx/tl for 30 sec, then cool down 4 C for 10 minutes with gentle shaking (cold room shaker).

6. Load paraffin tx/tl mix on top of 250 uL centrifuge buffer in 1.5 ml Eppendorf.

7. Centrifuge 3,000 g 20 min 4 C

8. Pipett liposomes

9. Wash liposomes 3× with (buffer)+300 mM sucrose, where (bufffer) is whatever your final reaction is in. Most of the time, that will be 50 mM HEPES pH 8. Wash step centrifugation: 1,500 g 5 min 4 C.

Optional: label membrane with 0.01% Rhodamine (Lissamine rhodamine B).

Centrifuge buffer: PBS with 150 mM sucrose

An alternative implementation of a protocol suitable for use in the method of an aspect of the invention is as follows:
Thin Film Preparation 1. Make stock of lipids in DCM or chloroform.

2. Aliquot 1 umole of lipid into each HPLC tube 3. evaporate overnight under the hood (cover with Al foil)

4. Store tubes in −20

For 20 samples of POPC: 15.2 mg POPC powder, dissolve in 4 ml solvent. Aliquot 200 uL into each HPLC tube.

For 20 samples of POPC:cholesterol 1:2: 15.2 mg POPC powder, 15.47 mg cholesterol powder, dissolve in 4 ml solvent. Aliquot 200 uL into each HPLC tube.

For 20 samples of POPC with 0.2 mol % rhodamine: 15.2 mg POPC powder, 0.053 mg rhodamine, 26.66 uL of 2 mg/ml stock, dissolve in 3.973 ml solvent. Aliquot 200 uL into each HPLC tube. POPC 1-Palmitoyl-2-oleoyl-sn-glycero-3-phosphocholine MW=760.1; cholesterol MW=386.65; Lissamine™ rhodamine B, stock 2 mg/ml, MW 1333.8.

For 20 samples of POPC with 0.2 mol % rhodamine: 15.2 mg POPC powder, 0.053 mg rhodamine, 26.66 uL of 2 mg/ml stock, dissolve in 3.973 ml solvent. Aliquot 200 uL into each HPLC tube.

Lipid-Oil Emulsion

5. Mix mineral oil by gentle inversion just before use.
6. Place 0.5 mL of mineral oil into the tube with lipid film.
7. Incubate the tube at 80° C. for ~15 min
8. Vortex for ~10 s
9. If the lipid film still remains, repeat steps 7 and 8.
10. Sonicate for 90 minutes in 60 C bath
11. After sonication, vortex again for 10 s
12. Incubate overnight at room temperature overnight.

Concentration of lipid in oil is 2 mM.

Making Liposomes

13. Mix lipid-oil mixture by vortexing immediately before use.
14. Add 10 uL of internal solution (Tris with calcein).
15. Vortex for ~15 sec
16. Load on top of 250 uL centrifuge buffer (PBS+150 mM sucrose)
17. Centrifuge 3,000 g 20 min 4 C
18. Pipett liposomes
19. Wash liposomes 3× with (buffer)+300 mM sucrose, where (bufffer) is whatever your final reaction is in. Most of the time, that will be 50 mM HEPES pH 8.

Wash step centrifugation: 1,500 g 5 min 4 C.

While two preferred protocols are described, it will be clear to one of skill in the art that other protocols are suitable, including but not limited to variations and modifications of the specific steps, materials, concentrations, and timings presented here.

Results from an Experimental Implementation of Synells

Figure 8:
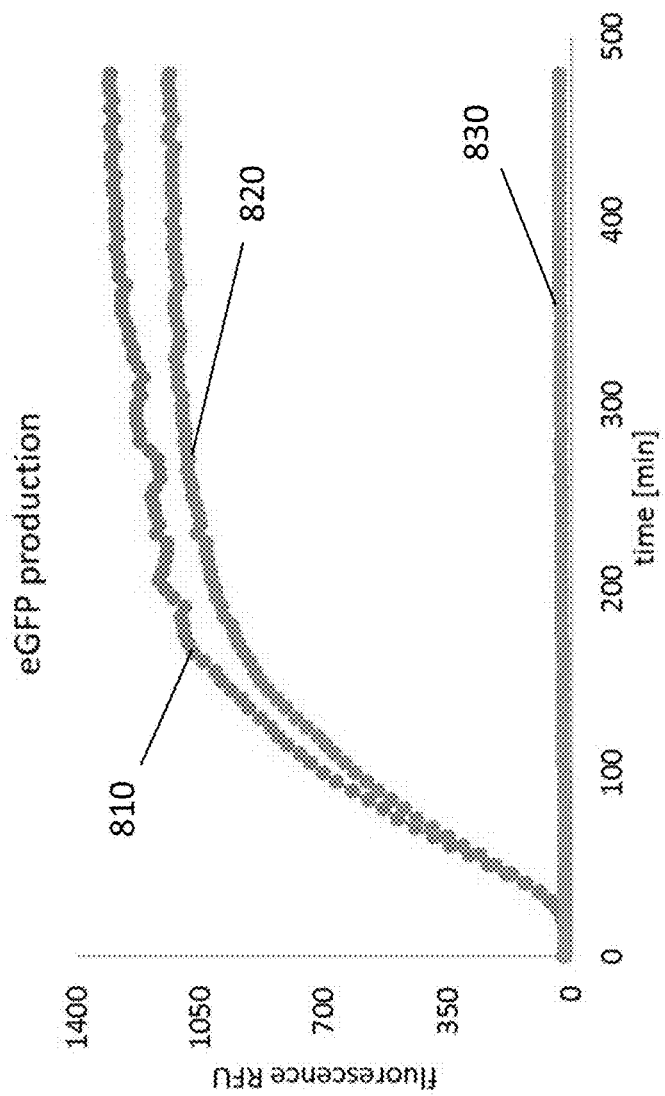
FIG. 8 is a graph of eGFP production in a bacterial cell-free protein expression reaction for an experimental implementation of synells according to one aspect of the invention.

FIG. 8 is a graph of eGFP production in a bacterial cell-free protein expression reaction for an experimental implementation of synells according to one aspect of the invention. Each positive control sample 810, 820 contains all protein expression system components, purified T7 polymerase, and the eGFP plasmid under T7 promoter control, as listed in Table 2. Negative control sample 830 contains the same enzyme mix as in Table 2, but without the plasmid.

TABLE 2

| Reagent | stock | Final in reaction | Units |
| --- | --- | --- | --- |
| Mg-glutamate (mM) | 1000 | 12 | mM |
| K-glutamate (mM) | 3000 | 140 | mM |
| DTT (mM) | 100 | 1 | mM |
| energy mix current energy mix | 10 | 1 | x |
| amino acids 20 mM stock | 20 | 2 | mM |
| plasmid | 200 | 20 | nM |
| RNAse inhibitor Murine 40,000 units/ml | | 0.3 uL, 12 units | |
| water to total | | | |
| Cell Free Prep | 3 | 1 | x |

Figure 9A:
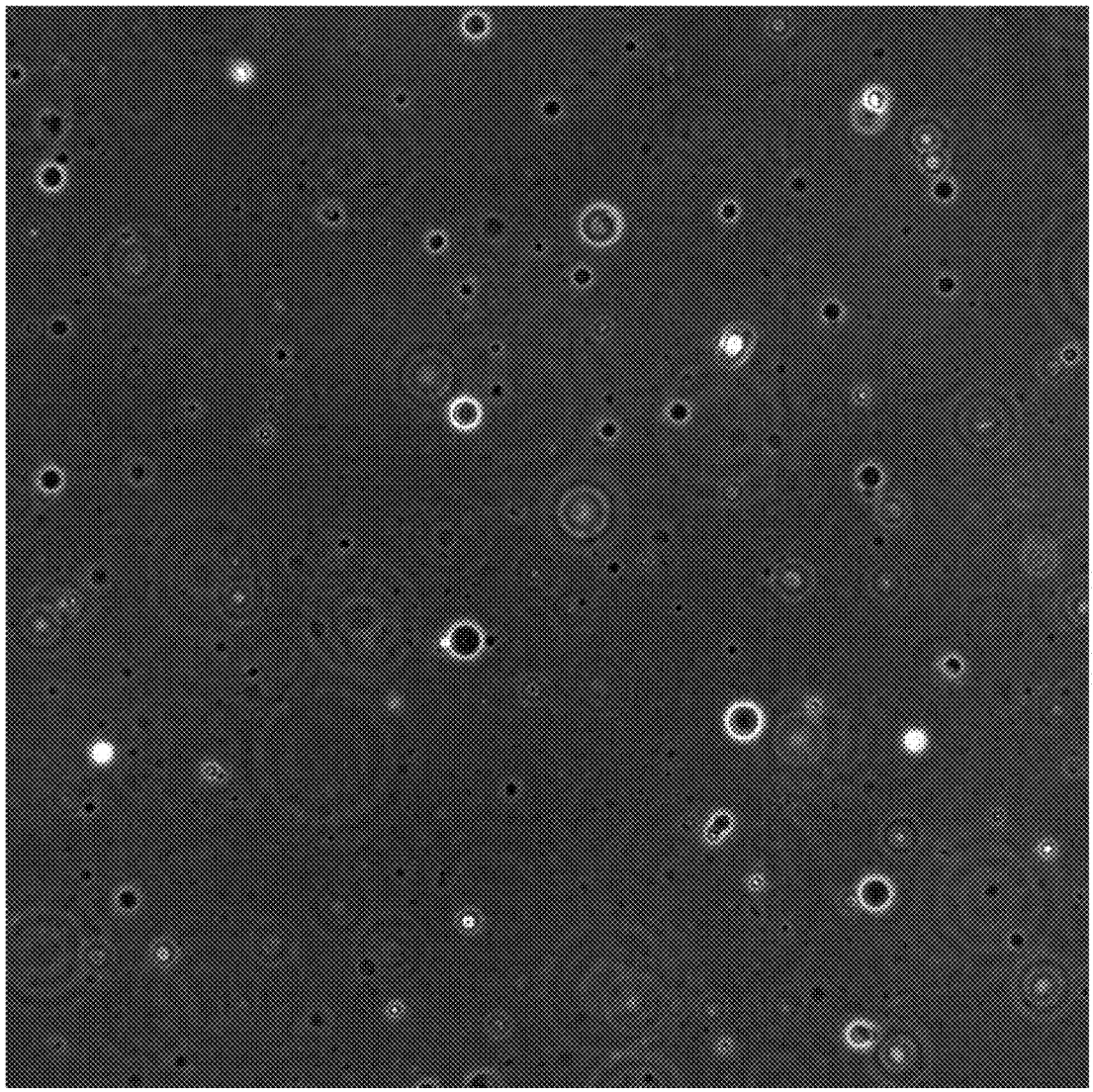
FIGS. 9A-C are images of a sample of synells containing the cell-free protein expression system of FIG. 8 encapsulated inside phospholipid liposomes, with FIG. 9A depicting phase contrast, FIG. 9B depicting GFP channel, and FIG. 9C depicting rhodamine channel.
Figure 9B:
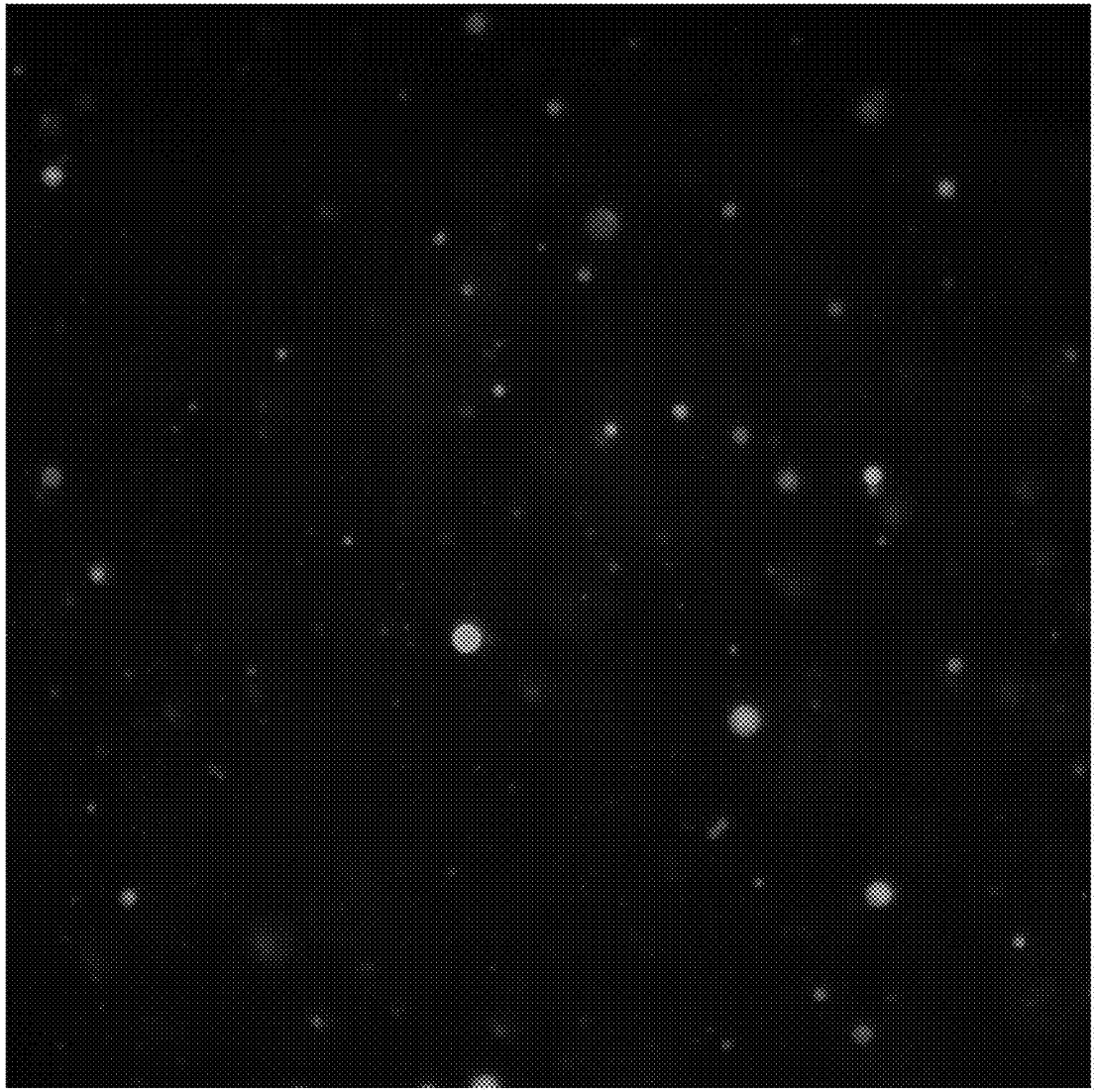
Figure 9C:
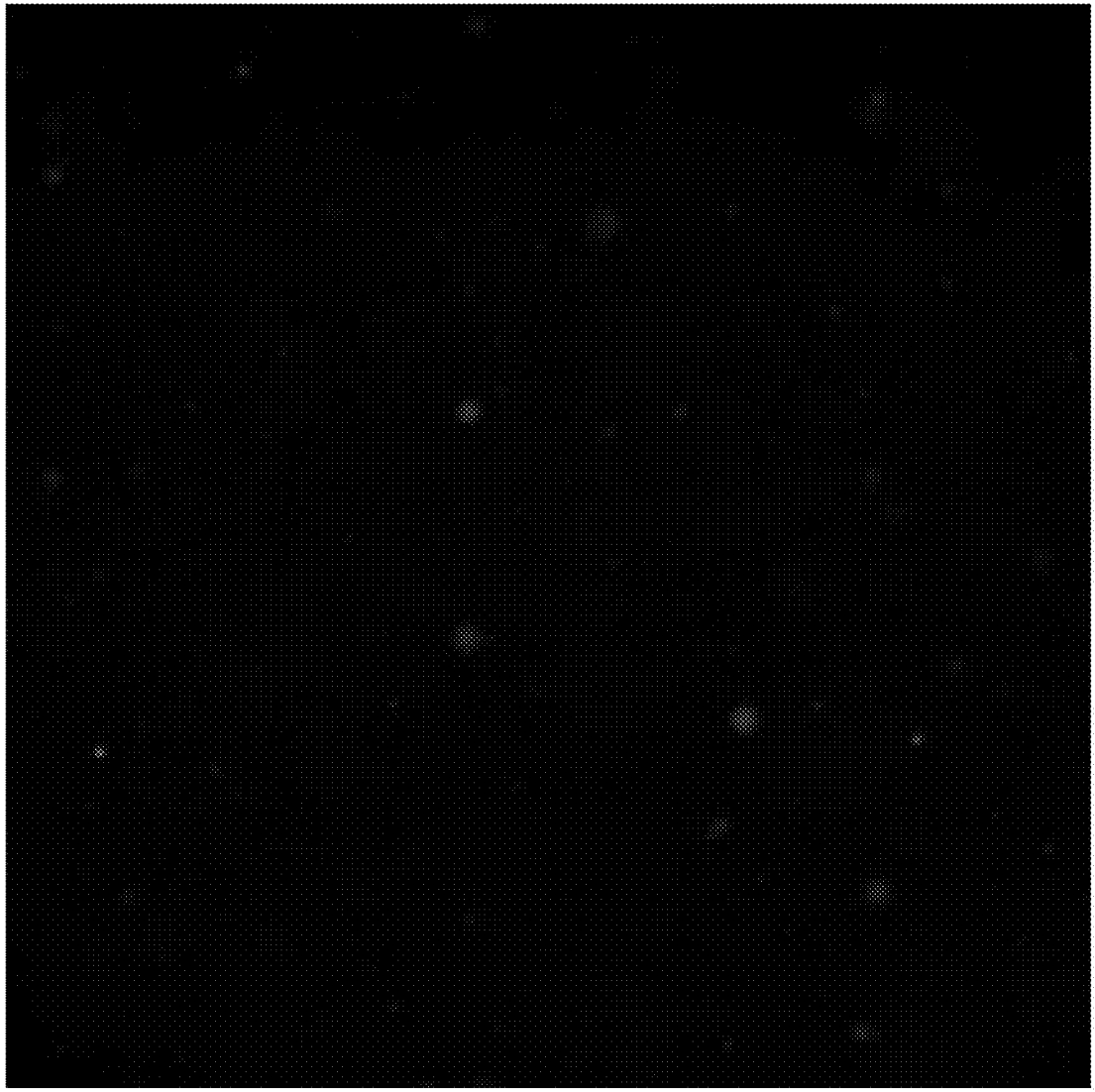
Figure 10A:
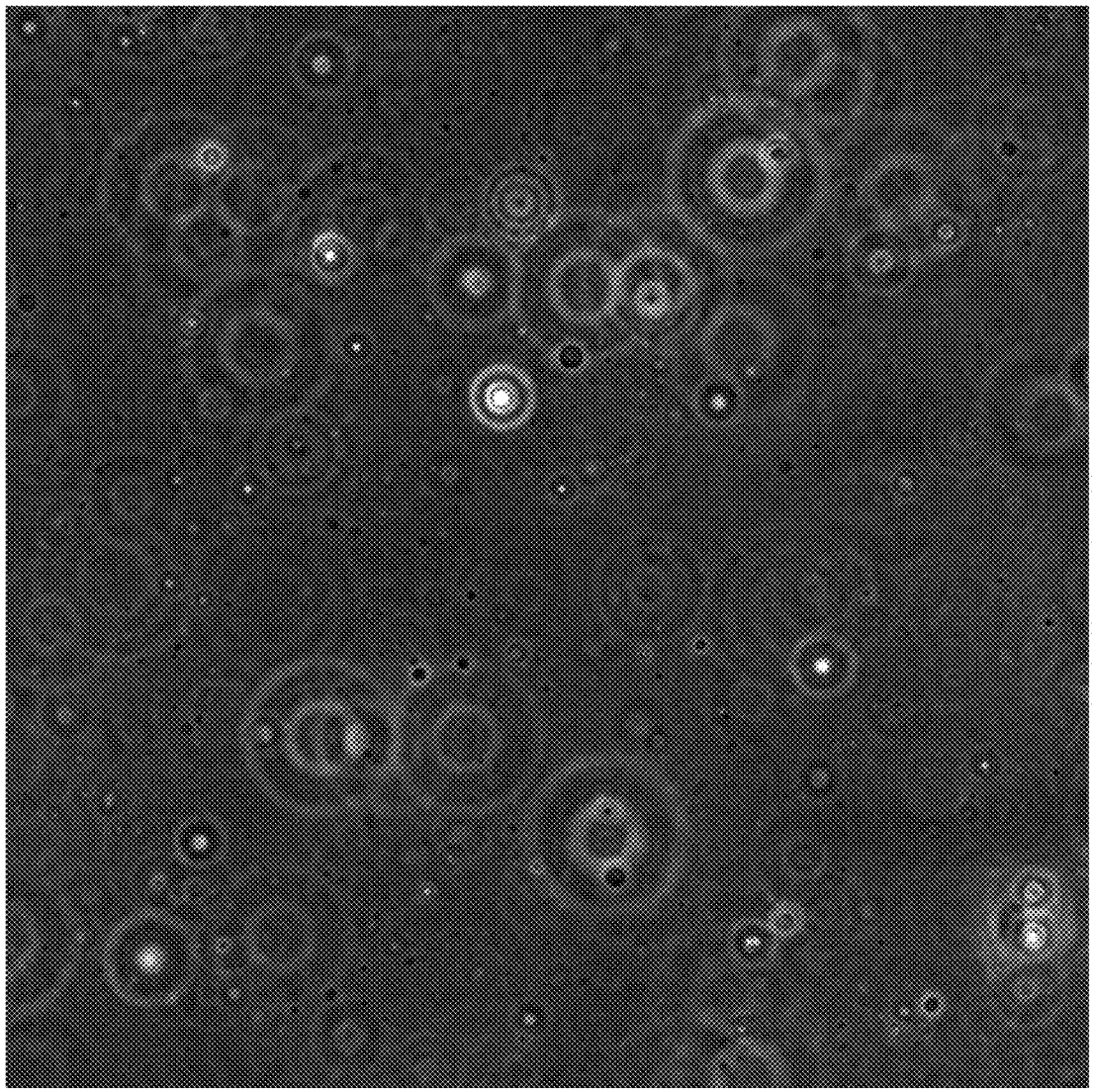
FIGS. 10A-C are images of a second sample of synells containing the cell-free protein expression system of FIG. 8 encapsulated inside phospholipid liposomes, with FIG. 10A depicting phase contrast, FIG. 10B depicting GFP channel, and FIG. 10C depicting rhodamine channel.
Figure 10B:
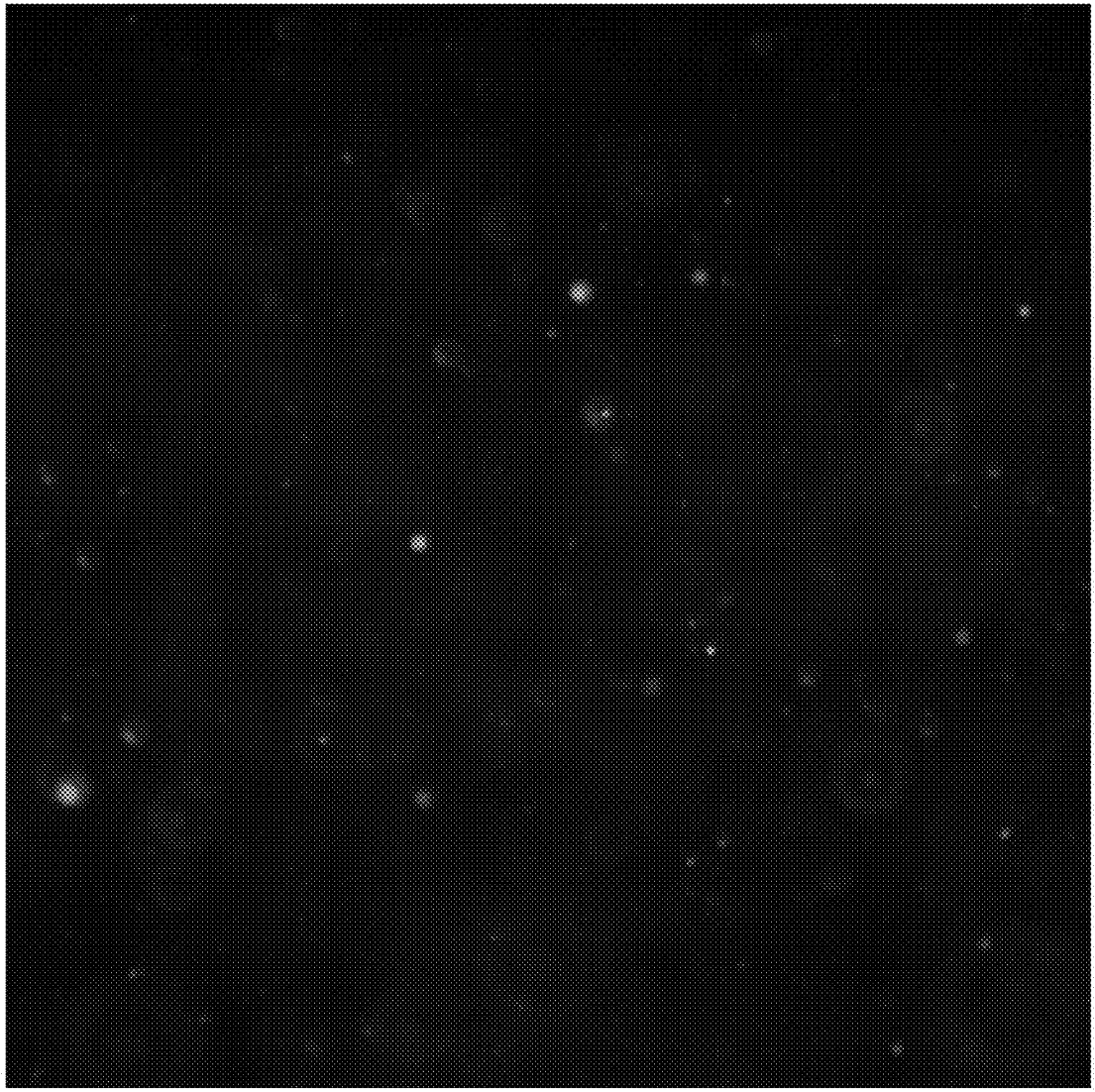
Figure 10C:
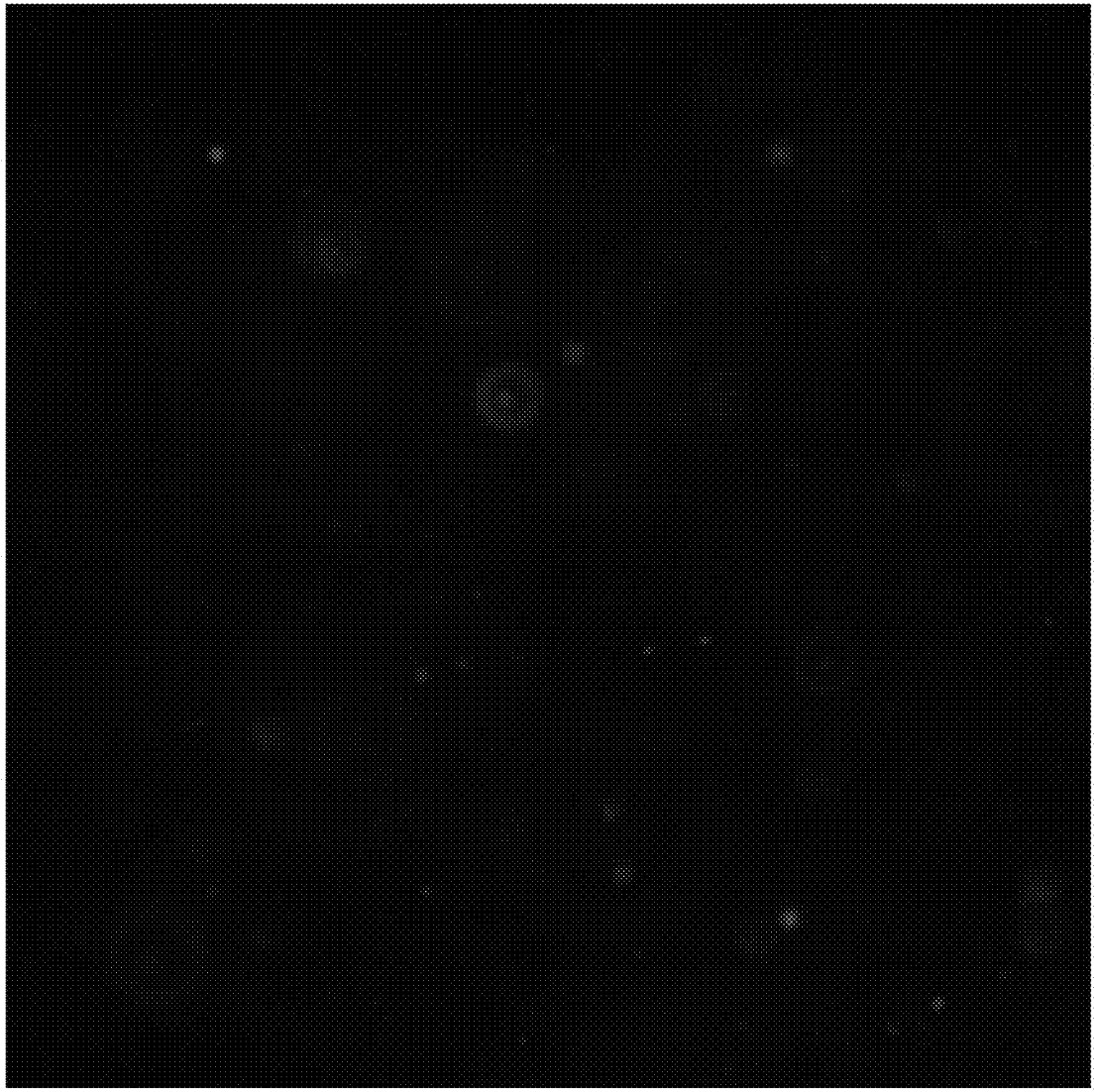

FIGS. 9A-C and 10A-C depict imaging results of synells containing this cell-free protein expression system, encapsulated inside phospholipid liposomes. Liposomes were labeled with 0.1 mol % of Lissamine Rhodamine B PE in order to visualize the membrane. Reaction time: 12 h. In particular, FIGS. 9A-C are images of Sample 1 810, phase contrast 40× (FIG. 9A), GFP channel 40× (FIG. 9B), and rhodamine channel 40× (FIG. 9C). FIGS. 10A-C are images of Sample 2 820, phase contrast 40× (FIG. 10A), GFP channel 40× (FIG. 10B), and rhodamine channel 40× (FIG. 10C).

The field of building synthetic cell chemical bioreactors has seen tremendous progress in the last few decades. This has enabled the development of better synell-based tools for a variety of novel research applications. Synells can be viewed as biochemical machines: fully programmable tools that are capable of serving as sensors, actuators, or controllers of biological systems, as well as interfacing between live cells and electronic systems. Synells with genetic circuit control mechanisms offer the possibility to develop new generations of "smart" bio-orthogonal and biodegradable sensors.

Synells can be used to study processes that are almost impossible to study in the complexity of a natural cell, such as formation of toxic species such as prions and protein fibrils, and this generalizable approach allows researchers to investigate mechanisms of toxicity and ask questions such as why some molecules are toxic in some contexts, concentrations, or mixtures, but not others, and how some natural cells remain unaffected while others are irreparably damaged. In addition to use in biological systems incompatible with live cells, synells permit the experimenter to deploy them in environments that are similarly incompatible. This could be of use for synells designed for specialized applications, like interfacing with electronics or biosensors and chemosensors in harsh environments. Unlike minimal cells derived from natural cells in a top-down process of genome reduction, synells also permit screening of random and semi-random combinations of components in isolated or interacting microfluidic chambers, enabling the possibility of screening vast numbers of individuals and ensembles of individuals interacting with each other in ways that are impossible with natural cells.

Other applications include interfacing synells and mammalian cells, digitizing biochemical assemblies, and using synells to model biological processes. Deployment of the present invention marks the creation of the new field of digital material biology. Using the present invention, it becomes possible, for the first time, to reproduce synthetic biology protocols with digital precision across labs with appropriately tuned equipment located across different continents or even planets. Chemostat and evoltant competitors may be set up for directed evolution and iterative optimization experiments in ways that are currently impossible to address experimentally. For instance: chirality in racemic mixtures, role of conformational states of identical sequence genetic material, stereocenters, specificity, potency, toxicity are encoded in catalytic steps that are obscure become reproducible and addressable with ensemble-physics methodology.

While preferred embodiments of the invention are disclosed herein, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. A method for creating ensembles of identical synells, comprising:
   creating a plurality of synells having a trait of interest, wherein each individual synell comprises a synell compartment encapsulating a plurality of synell components, wherein a synell component comprises a non-living molecular building block substance required for the synell to exhibit the trait of interest, wherein there are a plurality of types of synell components, wherein each synell component has been encapsulated and stored within a microfluidic device in at least one recorded location for that type of synell component, wherein the trait of interest comprises at least one of a particular synell function or composition, and wherein the trait of interest enables one or more biological or chemical reaction to take place within the synell, the step of creating comprising:
   within the microfluidic device, for each individual synell in the plurality of synells, retrieving, from among the stored type of synell components, a first type of synell component required for the trait of interest,
   encapsulating the first type of synell component within the synell compartment to create an intermediate synell;
   iteratively building each individual synell having the trait of interest by performing an iterative building cycle comprising the steps of:
      testing the intermediate synell for the presence of the first synell component;
      if the intermediate synell fails the test, removing the failed intermediate synell; and
      if the intermediate synell passes the test, retrieving and adding a second type of synell component to the intermediate synell, wherein the second type of synell component is different from the first type of synell component; and
   repeating the iterative building cycle by retrieving, adding, and testing for an additional different type of synell component during each cycle, until a synell having the trait of interest has been created.

2. The method of claim 1, wherein the iterative building cycle is under computer control.

3. The method of claim 1, wherein the iterative building cycle takes place according to a recipe for creation of the synell.

4. The method of claim 1, wherein the step of testing is carried out via flow cytometry.

5. The method of claim 1, wherein the step of adding employs at least one microfluidic droplet injector.

6. The method of claim 1, wherein the trait is synell function.

7. The method of claim 1, wherein the trait is synell composition.

8. The method of claim 1, wherein the synell compartment comprises a plurality of subcompartments and the method further comprises encapsulating at least one synell component within each subcompartment.

* * * * *